(12) United States Patent
Cines et al.

(10) Patent No.: US 7,939,063 B2
(45) Date of Patent: May 10, 2011

(54) DELIVERY VEHICLE FOR RECOMBINANT PROTEINS

(75) Inventors: Douglas B. Cines, Wynnewood, PA (US); Mortimer Poncz, Wynnewood, PA (US)

(73) Assignees: The Trustees of the University of Pennsylvania, Philadelphia, PA (US); The Children's Hospital of Philadelphia, Philadelphia, PA (US)

( * ) Notice: Subject to any disclaimer, the term of this patent is extended or adjusted under 35 U.S.C. 154(b) by 926 days.

(21) Appl. No.: 11/581,559

(22) Filed: Oct. 16, 2006

(65) Prior Publication Data

US 2007/0031392 A1    Feb. 8, 2007

Related U.S. Application Data

(62) Division of application No. 10/701,331, filed on Nov. 4, 2003, now abandoned.

(60) Provisional application No. 60/424,234, filed on Nov. 5, 2002.

(51) Int. Cl.
*A61K 48/00* (2006.01)
*A01N 63/00* (2006.01)
*C12P 21/06* (2006.01)
*C12N 5/00* (2006.01)
*C12N 15/00* (2006.01)
*C12N 15/11* (2006.01)

(52) U.S. Cl. .................. 424/93.72; 424/93.1; 424/93.2; 424/93.21; 424/93.7; 435/69.1; 435/320.1; 435/325; 435/455; 514/44 R

(58) Field of Classification Search .................. None
See application file for complete search history.

(56) References Cited

U.S. PATENT DOCUMENTS

| | | |
|---|---|---|
| 5,135,736 A | 8/1992 | Anderson et al. |
| 5,169,933 A | 12/1992 | Anderson et al. |
| 5,489,743 A | 2/1996 | Robinson et al. |
| 5,652,122 A | 7/1997 | Frankel et al. |
| 5,670,617 A | 9/1997 | Frankel et al. |
| 5,674,980 A | 10/1997 | Frankel et al. |
| 5,747,641 A | 5/1998 | Frankel et al. |
| 5,804,604 A | 9/1998 | Frankel et al. |
| 6,348,185 B1 | 2/2002 | Piwnica-Worms |

FOREIGN PATENT DOCUMENTS

| | | |
|---|---|---|
| WO | WO-92/06190 | 4/1992 |
| WO | WO-03/035697 | 5/2003 |
| WO | WO-03/035892 | 5/2003 |

OTHER PUBLICATIONS

Anderson, "Human Gene Therapy", Nature, 392:25-30 (Apr. 30, 1998).

Bdeir et al., "Urokinase mediates fibrinolysis in the pulmonary microvasculature", Blood, 96(5):1820-1826 (Sep. 1, 2000).

Booth et al., "Plasminogen activator inhibitor (PAI-1) in plasma and platelets", Brit. J. Haematol. 70:327-333 (Nov. 1988).

Booth et al., "Lysis of platelet-rich thrombi: the role of PAI-1", Ann. N. Y. Acad. Sci., 667:70-80 (Dec. 1992).

Chaloin et al., "Conformations of primary amphipathic carrier peptides in membrane mimicking environments", Biochem., 36(37):11179-11187 (Sep. 16, 1997).

Chaloin et al., "Design of carrier peptide-oligonucleotide conjugates with rapid membrane translocation and nuclear localization properties", Biochem. Biophys. Res. Commun., 243(2):601-608 (Feb. 13, 1998).

Couzin et al., "As Gelsinger Case Ends, Gene Therapy Suffers Another Blow", Science, 307:1028 (Feb. 18, 2005).

Declerck et al., "Measurement of plasminogen activator inhibitor 1 in biologic fluids with a murine monoclonal antibody-based enzyme-linked immunosorbent assay", Blood, 71:220-225 (Jan. 1998).

Fay et al., "Platelets inhibit fibrinolysis in vitro by both plasminogen activator inhibitor-1-dependent and -independent mechanisms", Blood, 83:351-356 (Jan. 15, 1994).

Fay et al., "Vitronectin inhibits the thrombotic response to arterial injury in mice", Blood, 93(6):1825-1830 (Mar. 15, 1999).

Futaki et al., "Structural variety of membrane permeable peptides", Curr. Protein Pept. Sci., 4(2):87-96 (Apr. 2003).

Futaki, "Arginine-rich peptides: potential for intracellular delivery of macromolecules and the mystery of the translocation mechanisms", Int. J. Pharm., 245(1-2):1-7 (Oct. 1, 2002).

Goncalves, "A Concise Peer Into the Background, Initial Thoughts, and Practices of Human Gene Therapy", Bioessays, 27(5):506-517 (2005).

Hayward et al, "Studies of a second family with the Quebec platelet disorder: evidence that the degradation of the alpha-granule membrane and its soluble contents are not secondary to a defect in targeting proteins to alpha-granules", Blood, 89:1243-1253 (Feb. 15, 1997).

Hayward et al., "Fibrinogen degradation products in patients with the Quebec platelet disorder", Brit. J. Haematol., 97:497-503 (May 1997).

(Continued)

*Primary Examiner* — Sumesh Kaushal
(74) *Attorney, Agent, or Firm* — Howson & Howson LLP

(57) ABSTRACT

Recombinant nucleic acid molecules are constructed with a first sequence encoding a transgene under the control of regulatory sequences that direct expression of the transgene product in a hematopoietic stem cell, or a progenitor cell therefrom or cell differentiated therefrom. In one embodiment, the cell which expresses the transgene is a secretory cell. The cell is a megakaryotic progenitor cell, or a cell further differentiated therefrom, such as a platelet. The cell is a granulocyte/macrophage progenitor cell or a cell further differentiated therefrom, such as a mast cell or neutrophils. Such host cells containing the molecule or the molecule itself are employed in methods for treating or preventing infection, inflammation or vascular injuries or any disorders involving or mediated by cells of the hematopoietic lineage.

4 Claims, 2 Drawing Sheets

OTHER PUBLICATIONS

Hayward et al., "An autosomal dominant, qualitative platelet disorder associated with multimerin deficiency, abnormalities in platelet factor V, thrombospondin, von Willebrand factor, and fibrinogen and an epinephrine aggregation defect", Blood, 87(12):4967-4978 (Jun. 15, 1996).

Holt et al., "Secretion of plasminogen by washed human platelets", Abstracts Circulation, 62(3):342, No. 1321 (Oct. 1980).

Holt et al., "Biochemistry of alpha granule proteins", Sem. Hematol., 22:151-163 (Apr. 1985).

Jiang et al., "Evidence for a novel binding protein to urokinase-type plasminogen activator in platelet membranes", Blood, 87:2775-2781 (Apr. 1, 1996).

Juengst, "What's Next for Human Gene Therapy", BMJ, 326:1410-1411 (Jun. 28, 2003).

Kahr et al., "Platelets from patients with the Quebec platelet disorder contain and secrete abnormal amounts of urokinase-type plasminogen activator", Blood, 98:257-265 (Jul. 15, 2001).

Kruithof et al., "Plasminogen activator inhibitor 1: development of a radioimmunoassay and observations on its plasma concentration during venous occlusion and after platelet aggregation", Blood, 70:1645-1653 (Nov. 1987).

Kufrin et al., "Antithrombotic thrombocytes: ectopic expression of urokinase-type plasminogen activator in platelets", Blood, 102(3):926-933 (Aug. 1, 2003).

Lenich et al., "Thrombin stimulation of platelets induces plasminogen activation mediated by endogenous urokinase-type plasminogen activator", Blood, 90:3579-3586 (Nov. 1, 1997).

Morris et al., "A peptide carrier for the delivery of biologically active proteins into mammalian cells", Nat. Biotechnol., 19(12):1173-1176 (Dec. 2001).

Ravid et al., "Targeted Expression of a Conditional Oncogene in Hematopoietic Cells of Transfenic Mice", J. Cell Biol. 123(6 Pt 1):1545-1553 (Dec. 1993).

Ravid et al., "Selective Targeting of Gene Products with the Megakaryocyte Platelet Factor 4 Promoteter", Proc. Natl. Acad Sci USA, 88(4):1521-1525 (Feb. 1991).

Rosenberg et al., "Gene Therapist, Heal Thyself", Science, 287:1751 (Mar. 10, 2000).

Taylor et al., "Delivery of bioactive, gel-isolated proteins into live cells", Electrophoresis, 24(9):1331-1337 (May 2003).

Touchette et al., "Gene Therapy: Not Ready for Prime Time", Nature Med., 2(1):7-8 (Jan. 1996).

Vives et al., "TAT peptide internalization: seeking the mechanism of entry", Curr. Protein Pept. Sci., 4(2):125-132 (Apr. 2003).

SEQUENCE LISTING

```
<160> NUMBER OF SEQ ID NOS: 6

<210> SEQ ID NO 1
<211> LENGTH: 26
<212> TYPE: DNA
<213> ORGANISM: Artificial
<220> FEATURE:
```

-continued

```
<223> OTHER INFORMATION: mouse PF4 5'UTR sense primer

<400> SEQUENCE: 1
cacttaagag ccctagaccc atttcc                                          26

<210> SEQ ID NO 2
<211> LENGTH: 21
<212> TYPE: DNA
<213> ORGANISM: Artificial
<220> FEATURE:
<223> OTHER INFORMATION: mouse u-PA exon 2 antisense primer

<400> SEQUENCE: 2
ttcagagttt ttcaccacca a                                               21

<210> SEQ ID NO 3
<211> LENGTH: 18
<212> TYPE: DNA
<213> ORGANISM: Artificial
<220> FEATURE:
<223> OTHER INFORMATION: mouse PF4 5'UTR sense primer

<400> SEQUENCE: 3
aattctcggg atctgggt                                                   18

<210> SEQ ID NO 4
<211> LENGTH: 19
<212> TYPE: DNA
<213> ORGANISM: Artificial
<220> FEATURE:
<223> OTHER INFORMATION: mouse u-PA exon 2 antisense primer

<400> SEQUENCE: 4
ctgggctcta gacagcagt                                                  19

<210> SEQ ID NO 5
<211> LENGTH: 17
<212> TYPE: DNA
<213> ORGANISM: Artificial
<220> FEATURE:
<223> OTHER INFORMATION: primer

<400> SEQUENCE: 5
gctggtgaaa aggacct                                                    17

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
cacaggacta gaacacctgc                                                 20
```

DELIVERY VEHICLE FOR RECOMBINANT PROTEINS

CROSS-REFERENCE TO RELATED INVENTIONS

This application is a divisional of U.S. patent application Ser. No. 10/701,331, filed Nov. 4, 2003, now abandoned which claims the benefit of the priority of U.S. Provisional Patent Application No. 60/424,234, filed Nov. 5, 2002.

STATEMENT REGARDING FEDERALLY SPONSORED RESEARCH OR DEVELOPMENT

The present invention was supported, in part, by the National Institutes of Health, Grant Nos. HL54749, HL64190, HL60169, HL66442, HL47826 and HL63194. The United States government has an interest in this invention.

BACKGROUND OF THE INVENTION

Hematopoietic stem cells are pluripotent cells present in the bone marrow, which divide to produce more specialized progenitor stem cells, i.e., lymphoid progenitors and myeloid progenitors. Cells that are differentiated from the lymphoid progenitors in the bone marrow and that are found in the peripheral blood include B cells and T cells. From B cells are generated plasma cells; from T cells are generated activated T cells. Similarly, the common myeloid progenitor stem cells produce the granulocytes/macrophage progenitor cells and the megakaryocyte/erythrocyte progenitor cells in the bone marrow. Cells differentiated from the granulocyte/macrophage progenitors that are present in the blood include neutrophils, eosinophils, basophils, monocytes and immature dendritic cells. Monocytes further give rise to mast cells, macrophages and dendritic cells that are present in tissue and lymph nodes. Cells differentiated from the megakaryocyte/erythrocyte progenitors include megakaryocytes and erythroblasts, which further differentiate into platelets and erythrocytes (red blood cells) in the blood.

A number of these hematopoietic lineage cells are secretory cells upon activation. For example, platelets, the smallest corpuscular components of human blood, are characterized by a diameter of about 2-4 micrometers, the absence of a nucleus, and a physiological number varying from 150,000 to 300,000 per cubic millimeter of blood. Platelets contribute to the complex, multistep, and highly regulated process of thrombus formation and arterial occlusive disorders, a leading cause of human morbidity. Platelets target and adhere to sites of vascular injury. At the sites of vascular injury, the platelets are activated and form aggregates that provide a provisional seal. Platelets preferentially release their granular contents at the site of injury, e.g., contributing to the subsequent growth and stability of thrombi in part through the release of von Willebrand factor (vWF), fibrinogen, and other coagulation proteins such as Factor V (Holt J. C., and Niewiarowski, S. 1985 *Sem. Hematol.* 22:151-163) from their alpha-granules. Activated platelets also release proteins that inhibit thrombolysis, chief among which is plasminogen activator inhibitor-1 (PAI-1). Over 90% of the circulating PAI-1 is stored in platelet alpha-granules (Booth, N. A et al, 1988 *Brit. J. Haematol.* 70:327-333), although much of this is in an inactive form (Declerck, P. J et al, 1988 *Blood* 71:220-225; Kruithof, E. K et al, 1987 *Blood* 70:1645-1653). Nonetheless, this pool of PAI-1 is thought to be one of the main reasons why platelet-rich thrombi are especially resistant to thrombolytic therapy (Booth, N. A et al, 1992 *Ann. N. Y. Acad. Sci.* 667:70-80; Fay, W. P. et al, 1994 *Blood* 83:351-356).

Paradoxically, platelets also contain or can bind small amounts of plasma-derived profibrinolytic proteins, including urokinase-type plasminogen activator (u-PA) and plasminogen (Fay, W. P et al, 1994 cited above; Lenich, C. et al, 1997 *Blood* 90:3579-3586; Jiang, Y et al. 1996 *Blood* 87:2775-2781; Holt, J. C., and Niewiarowski, S. 1980 *Circulation* 62:342a). However, these proteins are found at very low levels, and their activity is overwhelmed by the large amounts of PAI-1, which helps to stabilize nascent thrombi.

Recently, the effect of changing this balance in platelet fibrinolytic proteins has been described. Quebec Platelet Disorder (QPD) is a rare bleeding disorder not responsive to platelet transfusion, but responsive to anti-fibrinolytic agents, such as tranexamic acid (Hayward, C. P. et al, 1997 *Blood* 89:1243-1253; Hayward, C. P. et al, 1996 *Blood* 87:4967-4978; Hayward, C. P. et al, 1997 *Brit. J. Haematol.* 97:497-503). The etiology of QPD has been ascribed recently to ectopic expression of an excess of u-PA in megakaryocytes and platelets (Kahr, W. H. et al., 2001 *Blood* 98:257-265). QPD platelets contain predominantly activated two-chain urokinase (tcu-PA). The etiology for the bleeding diathesis may in part be due to local release of activated u-PA within thrombi leading to premature lysis. However, degradation of multiple platelet alpha-granular proteins, including vWF and Factor V, presumably by plasmin generated as a result of urokinase, may interfere with thrombus development as well.

There remains a need in the art for methods for harnessing the cellular mechanisms of platelets as well as other cells differentiated from hematopoietic progenitor cells for therapeutic, diagnostic and research purposes.

SUMMARY OF THE INVENTION

In one aspect, the invention provides a recombinant nucleic acid molecule comprising a first sequence encoding a transgene under the control of regulatory sequences that direct expression of the transgene product in a hematopoietic progenitor cell or a cell differentiated therefrom. In one embodiment, the cell that expresses the transgene is a secretory cell. In another embodiment, the cell is a lymphoid progenitor cell, a myeloid progenitor cell or a cell further differentiated therefrom, such as a platelet.

In another aspect, the invention provides a hematopoietic progenitor, lymphoid progenitor, or myeloid progenitor host cell transformed, transduced, infected or transfected with an above-described nucleic acid molecule.

In still another aspect, the invention provides a host cell differentiated from a progenitor cell that is transformed, transduced, infected or transfected with an above-described nucleic acid molecule.

In yet a further aspect, the invention provides a platelet transformed, transduced, infected or transfected with a nucleic acid molecule comprising a first sequence encoding a transgene, which is optionally a fibrinolytic protein, under the control of regulatory sequences that direct expression of the transgene in the platelet.

In a further aspect, the invention provides a method for generating a modified hematopoietic stem cell, a progenitor cell, or a modified cell differentiated from the hematopoietic stem cell and/or progenitor cell. The method involves transferring a nucleic acid molecule as described above into the cell via transformation, transduction, infection or transfection.

In yet another aspect, the invention provides methods for treating or preventing certain disorders, diseases, symptoms or injuries in which cells of the hematopoietic lineage are involved, by delivering to a mammalian patient a recombinant nucleic acid molecule described above or a suitable host cell described above, that contain a first sequence comprising a transgene encoding a product under the control of regulatory sequences that direct expression of the product of the transgene in the host cell. A differentiated cell produces the product at a suitable in the mammal.

In still a further aspect, the invention provides a method for preventing unwanted thrombus formation in a mammal by administering an above-described molecule or platelet containing same, in which the transgene is a fibrinolytic protein and the regulatory sequences direct expression of the product of the transgene in a platelet. The platelet produces the product at the site of the thrombus formation.

DETAILED DESCRIPTION OF THE INVENTION

Figure 1:
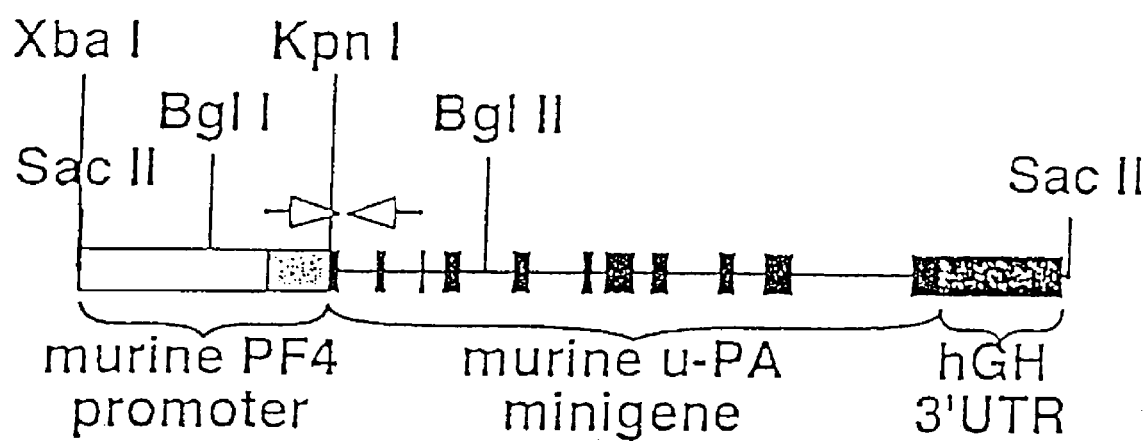
FIG. 1 is a schematic representation of the 10.2 kb Sac II insert obtained from the transgenic mice expressing u-PA in their platelets. The insert contains the 1.2 kb murine Xba I/Kpn I PF4 promoter (open box) plus a 5' untranslated region (5' UTR; light gray box) followed by the 11-exon murine u-PA gene (Heckel, J. L. et al, 1990 *Cell* 62:447-456, black boxes) and ending with the hGH 3'-UTR and polyadenylation sequence (dark gray box). The 2.8 kb Bgl II fragment containing the transgene was detected in a genomic Southern blot (not shown).

The present invention provides novel nucleic acid molecules, host cells containing the molecules, and methods for delivery of recombinant transgenes using modified cells of the hematopoietic stem cell lineage. Methods for treatment and prophylaxis using these cells are disclosed for a variety of disorders involving or mediated by the cells of the hematopoietic lineage. Such disorders can include inflammations, infections, tissue injuries, vascular injuries, and the like.

I. NUCLEIC ACID MOLECULES OF THE INVENTION

One aspect of this invention includes isolated, synthetic or recombinant nucleic acid molecules and sequences comprising a first sequence encoding a transgene under the control of regulatory sequences that direct expression of the transgene in a cell of the hematopoietic lineage. Such nucleic acid molecules are used to express the transgene product in vitro or ex vivo, or to permit expression of the transgene product in vivo in a mammal.

As used herein, the term "isolated nucleotide molecule or sequence" refers to a nucleic acid segment or fragment which is free from contamination with other biological components that are associated with the molecule or sequence in its natural environment. For example, one embodiment of an isolated nucleotide molecule or sequence of this invention is a sequence separated from sequences which flank it in a naturally occurring state, e.g., a DNA fragment which has been removed from the sequences which are normally adjacent to the fragment, such as the sequences adjacent to the fragment in a genome in which it naturally occurs. Further, the nucleotide sequences and molecules of this invention have been altered to encode a selected transgene product. Thus, the term "isolated nucleic acid molecule or sequence" also applies to nucleic acid sequences or molecules that have been substantially purified from other components that naturally accompany the unmutagenized nucleic acid, e.g., RNA or DNA, or proteins, in the cell. An isolated nucleotide molecule or sequence of this invention also encompasses sequences and molecules that have been prepared by other conventional methods, such as recombinant methods, synthetic methods, e.g., mutagenesis, or combinations of such methods. The nucleotide sequences or molecules of this invention should not be construed as being limited solely to the specific nucleotide sequences presented herein, but rather should be construed to include any and all nucleotide sequences which share homology (i.e., have sequence identity) with the nucleotide sequences presented herein.

By the term "promoter" or "regulatory sequence" is meant a DNA sequence required to direct expression of a nucleic acid operably linked thereto in a cell of hematopoietic lineage. Preferably the promoter/regulatory sequence is positioned at the 5' end of the transgene coding sequence such that it drives expression of the transgene-encoded protein in a cell. In the molecules of this invention, the promoter/regulatory sequence may also include an enhancer sequence and other regulatory elements that are required for expression in these hematopoietic cells.

Suitable regulatory sequences/promoters for use in the present invention are readily selected from among regulatory sequences that express the selected transgene in the hematopoietic stem cell itself, or in one of the progenitor cells of the hematopoietic lineage, including the common lymphoid progenitor, the common myeloid progenitor, the megakaryotic/erythrocyte progenitor or the granulocyte/macrophage progenitor. In one embodiment the regulatory sequences are able to direct expression of the transgene in a cell that is further differentiated from these progenitor cells. For example, suitable cells differentiated from the megakaryotic/erythrocyte progenitor cells are platelets, megakaryocytes or erythrocytes. Suitable cells differentiated from granulocyte/macrophage progenitor cells are neutrophils, eosinophils, monocytes, basophils and immature dendritic cells. Still other suitable cells differentiated from monocytes are mast cells, macrophages and dendritic cells. Suitable cells differentiated from said lymphoid progenitors are natural killer cells. Promoters capable of directing expression of a transgene in any of these cells of the hematopoietic lineage are useful as regulatory sequences in the nucleic acid molecules of this invention. In one embodiment, the promoter expresses the gene in secretory cells of the hematopoietic lineage, i.e., cells that release the contents of their granules upon activation, e.g., platelets, mast cells, neutrophils, eosinophils, etc. See, e.g., IMMUNOBIOLOGY, THE IMMUNE SYSTEM IN HEALTH AND DISEASE, 5$^{th}$ edit., C. Janeway et al., Ed., Garland Publishing, New York, N.Y.: 2001.

In one embodiment, a platelet-specific promoter is used as a regulatory sequence to direct expression of the transgene in a plasmid. Among suitable promoters are, without limitation, the Platelet factor 4 (PF4) promoter, the glycoprotein IIb promoter, the glycoprotein IIIa promoter, and the glycoprotein VI promoter. In another embodiment, the regulatory sequence is a neutrophil-specific promoter, such as one or more of the human neutrophil alpha defensin promoters DEFA1, DEFA2, DEFA3, and DEFA4, among others. Where the transgene is desirably expressed in a NK cell, the regulatory sequence is a natural killer cell-specific promoter, for example, the human perforin gene promoter. In still another embodiment, the regulatory sequence useful in the nucleic acid molecule of this invention is an eosinophil-specific promoter. Examples of eosinophil-specific promoters include, without limitation, the human eotaxin gene promoter and the eosinophil peroxidase gene promoter. In another embodiment, a suitable regulatory sequence is an erythrocyte-specific promoter, such as the human RhD gene promoter.

Depending upon the use for which the nucleic acid molecule is constructed, the transgene is any peptide, polypeptide or protein useful for the treatment of a disorder or reduction or prevention of a symptom in which cells of the hematopoietic system are involved. For example, a non-exclusive list of products includes those encoded by therapeutic transgenes for the treatment of a variety of inflammatory conditions, microbial or parasitic infections, injuries, such as vascular injuries and other hematopoietic cell-involved disorders. In one embodiment, such products include fibrinolytic proteins, including without limitation, urokinase-type plasminogen activator, plasminogen activator inhibitor-1 (PAI-1), von Willebrand factor, fibrinogen, Factor V, and plasminogen for use in altering the hemostatic balance at sites of thrombosis. Suitable products also include, without limitation, hormones and growth and differentiation factors including, without limitation, insulin, glucagon, growth hormone (GH), parathyroid hormone (PTH), growth hormone releasing factor (GHRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), any one of the transforming growth factor β superfamily, including TGF β, activins, inhibins, or any of the bone morphogenic proteins (BMP) including BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, IL-2, IL-4, IL-12, and IL-18), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitation, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, and the scavenger receptor. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD, myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence.

Still other useful gene products include enzymes such as are useful in enzyme replacement therapy, which is useful in a variety of conditions resulting from deficient activity of enzyme.

Further useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene are particularly desirable for treatment of hyperproliferative conditions characterized by hyperproliferating cells, as are cancers and psoriasis. Some polypeptides, which are produced exclusively or at higher levels in hyperproliferative cells as compared to normal cells. The compositions of this invention are employed to express as transgene products polypeptides that can reduce the activity or inactivate oncogenes such as myb, myc, fyn, and the translocation gene bcr/abl, ras, src, P53, neu, trk and EGRF. Anti-cancer treatments and protective regimens include transgene products directed to inactivate or reduce the activity of variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides, which are found at higher levels in tumor cells including the polypeptide recognized by monoclonal antibody 17-1A and folate binding polypeptides.

Other suitable therapeutic polypeptides and proteins include those which are useful for treating individuals suffering from autoimmune diseases and disorders by conferring a broad based protective immune response against targets that are associated with autoimmunity including cell receptors and cells which produce "self"-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

Still other suitable transgenes encode fibrinolytic proteins and peptides suitable for delivery by transgene expression in platelets, such as illustrated in the below-noted examples. The selection of the transgene sequence, or other molecule carried by the nucleic acid molecule, is not a limitation of this invention. Choice of a transgene sequence is within the skill of the artisan in accordance with the teachings of this application.

The terms "homology" or "similarity," when referring to a nucleic acid or fragment thereof, indicate that, when optimally aligned with appropriate nucleotide insertions or deletions with another nucleic acid (or its complementary strand), there is nucleotide sequence identity in at least about 70% of the nucleotide bases, as measured by any well-known algorithm of sequence identity, such as FASTA, a program in GCG Version 6.1. The term "homologous" as used herein, refers to the sequence similarity between two polymeric molecules, e.g., between two nucleic acid molecules, e.g., two DNA molecules, two RNA molecules, or two polypeptide molecules. When a nucleotide or amino acid position in both of the two molecules is occupied by the same monomeric nucleotide or amino acid, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous, then the two sequences are 50% homologous. If 90% of the positions, e.g., 9 of 10, are matched or homologous, the two sequences share 90% homology. By way of example, the DNA sequences 3'ATTGCC5' and 3'TATGCG5' share 50% homology. By the term "substantially homologous" as used herein, is meant DNA or RNA which is about 70% homologous, more preferably about 80% homologous, and most preferably about 90% homologous to the desired nucleic acid.

When referring to the transgenes or the regulatory sequences disclosed above, the invention is also directed to an isolated nucleotide molecule comprising a nucleic acid sequence that is at least 70%, 80% or 90% homologous to a nucleic acid sequence encoding a naturally occurring transgene-encoded protein or a polypeptide that has similar biological effect as the native transgene product. Furthermore, due to the degeneracy of the genetic code, any three-nucleotide codon that encodes a mutant or substituted amino acid residue of a transgene-encoded protein, described herein is within the scope of the invention.

Where, as discussed herein, proteins, and/or DNA sequences encoding them, or other sequences useful in nucleic acid molecules or compositions described herein are defined by their percent homologies or identities to identified sequences, the algorithms used to calculate the percent homologies or percent identities include the following: the Smith-Waterman algorithm (J. F. Collins et al, 1988, *Comput. Appl. Biosci.*, 4:67-72; J. F. Collins et al, Molecular Sequence Comparison and Alignment, (M. J. Bishop et al, eds.) In Practical Approach Series: Nucleic Acid and Protein Sequence Analysis XVIII, IRL Press: Oxford, England, UK (1987) pp. 417), and the BLAST and FASTA programs (E. G. Shpaer et al, 1996, *Genomics*, 38:179-191). These references are incorporated herein by reference.

By describing two DNA sequences as being "operably linked" as in the relationship between the transgene and the regulatory sequences used herein, is meant that a single-stranded or double-stranded DNA comprises two DNA sequences and that the two DNA sequences are arranged within the molecule or sequence in such a manner that at least one of the DNA sequences is able to exert a physiological effect by which it is characterized upon the other.

Preferably, each protein encoding transgene sequence and necessary regulatory sequences of this invention are present in a separate viral or non-viral recombinant vector (including non-viral methods of delivery of a nucleic acid molecule into a cell). Alternatively, two or more of these nucleic acid sequences encoding duplicate copies of a the transgene-encoded protein or encoding multiple different therapeutic proteins of this invention are contained in a polycistronic transcript, i.e., a single molecule designed to express multiple gene products.

The isolated nucleic acid of this invention is desirably a recombinant vector, particularly a plasmid, containing isolated and purified DNA sequences comprising DNA sequences that encode a selected therapeutic protein. By the term "vector" as used herein, is meant a DNA molecule derived from viral or non-viral, e.g., bacterial, species that has been designed to encode an exogenous or heterologous nucleic acid sequence. Thus, the term includes conventional bacterial plasmids. Such plasmids or vectors can include plasmid sequences from viruses or phages. Such vectors include chromosomal, episomal and virus-derived vectors, e.g., vectors derived from bacterial plasmids, bacteriophages, yeast episomes, yeast chromosomal elements, and viruses. Vectors may also be derived from combinations thereof, such as those derived from plasmid and bacteriophage genetic elements, cosmids, and phagemids. The term also includes non-replicating viruses that transfer a gene from one cell to another. The term should also be construed to include non-plasmid and non-viral compounds which facilitate transfer of nucleic acid into cells, such as, for example, polylysine compounds and the like.

The nucleic acid molecules of the invention include non-viral vectors or methods for delivery of the sequences encoding the therapeutic protein to a host cell according to this invention. A variety of non-viral vectors are known in the art and may include, without limitation, plasmids, bacterial vectors, bacteriophage vectors, "naked" DNA and DNA condensed with cationic lipids or polymers.

Examples of bacterial vectors include, but are not limited to, sequences derived from *bacille Calmette Guérin* (BCG), *Salmonella, Shigella, E. coli*, and *Listeria*, among others. Suitable plasmid vectors include, for example, pBR322, pBR325, pACYC177, pACYC184, pUC8, pUC9, pUC18, pUC19, pLG339, pR290, pK37, pKC101, pAC105, pVA51, pKH47, pUB110, pMB9, pBR325, Col E1, pSC101, pBR313, pML21, RSF2124, pCR1, RP4, pBAD18, and pBR328. Examples of suitable inducible *Escherichia coli* expression vectors include pTrc (Amann et al., 1988 *Gene*, 69:301-315), the arabinose expression vectors (e.g., pBAD18, Guzman et al, 1995 *J. Bacteriol.*, 177:4121-4130), and pETIId (Studier et al., 1990 *Methods in Enzymology*, 185:60-89).

Another type of useful vector is a single or double-stranded bacteriophage vector. For example, a suitable cloning vector includes, but is not limited to the vectors such as bacteriophage λ vector system, λgt11, μgt μWES.tB, Charon 4, λgt- WES-λB, Charon 28, Charon 4A, λgt-1-λBC, λgt-1-λB, M13mp7, M13mp8, or M13mp9, among others.

In yet another embodiment, a mammalian expression vector is used for expression of the selected transgene in mammalian cells of the hematopoietic lineage. Examples of mammalian expression vectors include pCDM8 (Seed, 1987 *Nature*, 329:840-842) and pMT2PC (Kaufman et al., 1987 *EMBO J.*, 6(1):187-93). When used in mammalian cells, the expression vector's control functions are often provided by viral regulatory elements other than the promoters specified above.

One type of recombinant vector is a recombinant single or double-stranded RNA or DNA viral vector. A variety of viral vector systems are known in the art. Examples of such vectors include, without limitation, recombinant adenoviral vectors, herpes simplex virus (HSV)-based vectors, adeno-associated viral (AAV) vectors, hybrid adenoviral/AAV vectors, recombinant retroviruses or lentiviruses, recombinant poxvirus vectors, recombinant vaccinia virus vectors, SV-40 vectors, insect viruses such as baculoviruses, and the like that are constructed to carry or express a selected nucleic acid composition of interest.

Retrovirus vectors that can be employed include those described in EP 0 415 731; International Patent Publication Nos. WO 90/07936; WO 94/03622; WO 93/25698; and WO 93/25234; U.S. Pat. No. 5,219,740; International Patent Publication Nos. WO 93/11230 and WO 93/10218; Vile and Hart, 1993 *Cancer Res.* 53:3860-3864; Vile and Hart, 1993 *Cancer Res.* 53:962-967; Ram et al., 1993 *Cancer Res.* 53:83-88; Takamiya et al., 1992 *J. Neurosci. Res.* 33:493-503; Baba et al., 1993 *J. Neurosurg.* 79:729-735; U.S. Pat. No. 4,777,127; GB Patent No. 2,200,651; and EP 0 345 242. Examples of suitable recombinant retroviruses include those described in International Patent Publication No. WO 91/02805. See also, D. A. Wilcox et al, 2000 Blood, 95 (12):3645-3652.

Alphavirus-based vectors may also be used as the nucleic acid molecule encoding the therapeutic protein. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and International Patent Publication Nos. WO 92/10578; WO 94/21792; WO 95/27069; WO 95/27044; and WO 95/07994.

Examples of adenoviral vectors include those described by Berkner, 1988 *Biotechniques* 6:616-627; Rosenfeld et al., 1991 *Science* 252:431-434; International Patent Publication No. WO 93/19191; Kolls et al., 1994 *PNAS* 91:215-219; Kass-Eisler et al., 1993 *PNAS* 90:11498-11502; Guzman et al., 1993 *Circulation* 88:2838-2848; Guzman et al., 1993 *Cir. Res.* 73:1202-1207; Zabner et al., 1993 *Cell* 75:207-216; Li et al., 1993 *Hum. Gene Ther.* 4:403-409; Cailaud et al., 1993 *Eur. J. Neurosci.* 5:1287-1291; Vincent et al., 1993 *Nat. Genet.* 5:130-134; Jaffe et al., 1992 *Nat. Genet.* 1:372-378; and Levrero et al., 1991 *Gene* 101:195-202. Exemplary adenoviral vectors include those described in International Patent Publication Nos. WO 94/12649; WO 93/03769; WO 93/19191; WO 94/28938; WO 95/11984 and WO 95/00655. Other adenoviral vectors include those derived from chimpanzee adenoviruses, such as those described in U.S. Pat. No. 6,083,716.

Another viral vector is based on a parvovirus such as an adeno-associated virus (AAV). Representative examples include the AAV vectors described in International Patent Publication No. WO 93/09239, Samulski et al., 1989 *J. Virol.* 63:3822-3828; Mendelson et al., 1988 *Virol.* 166:154-165; and Flotte et al., 1993 *PNAS* 90:10613-10617. Other particularly desirable AAV vectors include those based upon AAV1; see, International Patent Publication No. WO 00/28061, published May 18, 2000. Other desirable AAV vectors include those which are pseudotyped, i.e., contain a minigene composed of AAV 5' ITRs, a transgene, and AAV 3' ITRs packaged in a capsid of an AAV serotype heterologous to the AAV ITRs. Methods of producing such pseudotyped AAV vectors are described in detail in International Patent Publication No. WO01/83692.

In an embodiment in which the nucleic acid molecule of the invention is "naked DNA", it is combined with polymers including traditional polymers and non-traditional polymers such as cyclodextrin-containing polymers and protective, interactive noncondensing polymers, among others. The "naked" DNA and DNA condensed with cationic lipids or polymers are typically delivered to the cells using chemical methods. A number of chemical methods are known in the art for cell delivery and include using lipids, polymers, or proteins to complex with DNA, optionally condensing the same into particles, and delivering to the cells. Another non-viral chemical method includes using cations to condense DNA, which is then placed in a liposome and used according to the present invention. See, C. Henry, 2001 *Chemical and Engineering News*, 79(48):35-41.

The nucleic acid molecule encoding the selected therapeutic protein is introduced directly into the cells of the hematopoietic lineage either as "naked" DNA (U.S. Pat. No. 5,580,859) or formulated in compositions with agents that facilitate direct immunization, such as bupivacaine and other local anesthetics (U.S. Pat. No. 6,127,170).

All components of the viral and non-viral vectors above are readily selected from among known materials in the art and available from the pharmaceutical industry. Selection of the vector components other than the regulatory sequences are not considered a limitation on this invention. Each nucleic acid sequence encoding a protein according to this invention is preferably under the control of regulatory sequences that direct the replication and generation of the product of each nucleic acid sequence, preferably ectopically, in a mammalian hematopoietic lineage, progenitor cell or differentiated cell.

Additional regulatory sequences for inclusion in a nucleic acid sequence, molecule or vector of this invention include, without limitation, one or more of an enhancer sequence, a polyadenylation sequence, a splice donor sequence and a splice acceptor sequence, a site for transcription initiation and termination positioned at the beginning and end, respectively, of the polypeptide to be translated, a ribosome binding site for translation in the transcribed region, an epitope tag, a nuclear localization sequence, an IRES element, a Goldberg-Hogness "TATA" element, a restriction enzyme cleavage site, a selectable marker and the like. Enhancer sequences include, e.g., the 72 bp tandem repeat of SV40 DNA or the retroviral long terminal repeats or LTRs, etc. and are employed to increase transcriptional efficiency. Selection of other non-promoter common vector elements is conventional and many such sequences are available with which to design the nucleotide molecules and vectors useful in this invention. See, e.g., Sambrook et al, *Molecular Cloning. A Laboratory Manual*, Cold Spring Harbor Laboratory, New York, (1989) and references cited therein at, for example, pages 3.18-3.26 and 16.17-16.27 and Ausubel et al., *Current Protocols in Molecular Biology*, John Wiley & Sons, New York (1989). One of skill in the art may readily select from among such known non-promoter sequences to prepare nucleic acid molecules of this invention. The selection of such non-promoter sequences is not a limitation of this invention.

II. METHODS OF PRODUCING THE NUCLEIC ACID MOLECULES

The preparation or synthesis of the nucleotide sequences and nucleotide molecules of this invention is well within the ability of the person having ordinary skill in the art using available material. The synthesis methods are not a limitation of this invention. The examples below detail presently preferred embodiments of synthesis of sequences encoding an exemplary transgene useful in this invention for the construction of a transgenic animal model. However, similar methods are employed to produce nucleic acid molecules for the generation of therapeutic or prophylactic compositions of this invention.

The nucleotide molecules and sequences of this invention are produced by chemical synthesis methods. For example, the nucleotide sequences useful in the invention are prepared conventionally by resort to known chemical synthesis techniques, e.g., solid-phase chemical synthesis, such as described by Merrifield, 1963 *J. Amer. Chem. Soc.,* 85:2149-2154; J. Stuart and J. Young, Solid Phase Peptide Synthesis, Pierce Chemical Company, Rockford, Ill. (1984); Matteucci et al., 1981 *J. Am. Chem. Soc.,* 103:3185; Alvarado-Urbina et al., 1980 *Science,* 214:270; and Sinha, N. D. et al., 1984 *Nucl. Acids Res.,* 13:4539, among others. See, also, e.g., PROTEINS—STRUCTURE AND MOLECULAR PROPERTIES, 2nd Ed., T. E. Creighton, W.H. Freeman and Company, New York, 1993; Wold, F., "Posttranslational Protein Modifications: Perspectives and Prospects", pgs. 1-12 in POST-TRANSLATIONAL COVALENT MODIFICATION OF PROTEINS, B. C. Johnson, Ed., Academic Press, New York, 1983; Seifter et al., 1990 *Meth. Enzymol.,* 182:626-646, and Rattan et al., 1992 *Ann. N.Y. Acad. Sci.,* 663:48-62.

Alternatively, the nucleic acid molecules of this invention are constructed recombinantly using conventional molecular biology techniques, site-directed mutagenesis, genetic engineering or polymerase chain reaction, such as, by cloning and expressing a nucleotide molecule encoding a desired therapeutic protein with optional other proteins within a host cell of the hematopoietic lineage, etc. utilizing the information provided herein (See, e.g., Sambrook et al., cited above; Ausubel et al. cited above). Coding sequences for the transgenes and the regulatory sequences can be prepared synthetically (W. P. C. Stemmer et al, 1995 *Gene,* 164:49).

In general, recombinant DNA techniques involve obtaining by synthesis or isolation a DNA sequence that encodes the desired therapeutic protein as described above, and introducing it into an appropriate vector where it is expressed preferably under the control of the selected promoter that can direct expression in a cell of the hematopoietic lineage.

Any of the methods described for the insertion of DNA into a vector is used to ligate the selected promoter and other regulatory control elements into specific sites within the selected recombinant vector to generate the nucleic acid molecule.

III. HOST CELLS OF THE INVENTION

In another aspect of this invention, a cell of the hematopoietic lineage is manipulated to contain a nucleic acid molecule described above.

In one embodiment, the nucleic acid molecule generated as described above is transferred into an isolated hematopoietic stem cell, a common lymphoid progenitor cell, a common myeloid progenitor cell, a megakaryotic/erythrocyte progenitor cell or a granulocyte/macrophage progenitor cell. The hematopoietic stem cells or progenitor cells of the hematopoietic lineage are isolated from bone marrow of a suitable human or non-human mammal. For example, the cells are isolated from a mammalian patient into whom the manipulated cells are re-introduced. Alternatively, the mammal providing the host cells is a different mammal, for either introduction into another mammal or for research or laboratory use. Methods for isolating such cells from bone marrow are well known. See, for example, the Stem Cell Database of Princeton University; Phillips, R L et al, 2000 Science, 288: 1635-1640 and references cited therein.

In another embodiment, the host cells of the hematopoietic lineage are those cells found in the peripheral blood or tissue, such as platelets, megakaryocytes, neutrophils, eosinophils, monocytes, basophils, dendritic cells, mast cells, macrophages, dendritic cells, erythrocytes, and natural killer cells. These cells must be isolated from the peripheral blood or tissue of a suitable human or non-human mammal. For example, the cells are isolated from a mammalian patient into whom the manipulated cells would be re-introduced. Alternatively, the mammal providing the host cells is a different mammal, for either introduction into another mammal or for research or laboratory use. Methods for isolating such cells from peripheral blood or tissue are well known. The introduction of a platelet expressing a suitable transgene under the platelet specific PF4 regulatory sequence is exemplified in the examples below.

Once the suitable host cell is isolated, the nucleic acid molecule or vector is transferred therein in vitro or ex vivo by a conventional technique such as transformation, transduction, infection or transfection. The selection of other suitable methods for transferring the nucleic acid molecule or the vector into an isolated cell of the hematopoietic lineage can be performed by one of skill in the art by reference to known techniques. See, e.g., Gething and Sambrook, 1981 *Nature,* 293:620-625, among others.

If necessary, such host cells are cultured. Culture conditions are well known in the art and include ionic composition and concentration, temperature, pH and the like. Typically, transfected cells are maintained under culture conditions in a culture medium. Suitable media for various cell types are well known in the art. In a preferred embodiment, the temperature is from about 20° C. to about 50° C., more preferably from about 30° C. to about 40° C. and, even more preferably about 37° C.

The pH is preferably from about a value of 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/l and, more preferably from about 290 mosm/L to about 310 mosm/L. Other biological conditions needed for transfection of a vector are well known in the art.

IV. METHODS OF USE OF THE NUCLEIC ACID COMPOSITION AND HOST CELLS OF THE INVENTION

Once transfected, the host cells of the hematopoietic lineage are employed in pharmaceutical or prophylactic compositions and methods for the treatment of a variety of disorders in human or non-human mammals. Such treatment may include enhancement of a biological activity or reduction or a disadvantageous biological activity occurring in the body. Similarly, the nucleic acid molecules themselves are used in direct treatment of disorders such as inflammatory disorders, microbial or parasitic infection, vascular or hemorrhagic disorders, and the like in which the hematopoietic cells, their progenitors or differentiated cells are implicated. In other embodiments, the host cells (preferably platelets) are employed to prevent formation of stable, occlusive thrombus development.

One of skill in the art may readily identify a number of such disorders. Among such disorders are included without limitation, coagulation disorders (either an insufficiency or excess thereof), acute lung injury and sepsis, helminth infection, asthma or other allergic reactions, viral infections, bacterial infections, etc. For example, the compositions of this invention are useful in the prevention and/or treatment of disease(s) caused by microbial infections including, without limitation, *Haemophilus influenzae* (both typable and nontypable), *Haemophilus somnus, Moraxella catarrhalis, Streptococcus pneumoniae, Streptococcus pyogenes, Streptococcus agalactiae, Streptococcus faecalis, Helicobacter pylori, Neisseria meningitidis, Neisseria gonorrhoeae, Chlamydia trachomatis, Chlamydia pneumoniae, Chlamydia psittaci, Bordetella pertussis, Alloiococcus otiditis, Salmonella typhi, Salmonella typhimurium, Salmonella choleraesuis, Escherichia coli, Shigella, Vibrio cholerae, Corynebacterium diphtheriae, Mycobacterium tuberculosis, Mycobacterium avium-Mycobacterium intracellulare* complex, *Proteus mirabilis, Proteus vulgaris, Staphylococcus aureus, Staphylococcus epidermidis, Clostridium tetani, Leptospira interrogans, Borrelia burgdorferi, Pasteurella haemolytica, Pasteurella multocida, Actinobacillus pleuropneumoniae* and *Mycoplasma gallisepticum.*

The compositions of this invention are useful in the prevention and/or treatment of disease caused by, without limitation, Respiratory syncytial virus, Parainfluenza virus types 1-3, Human metapneumovirus, Influenza virus, Herpes simplex virus, Human cytomegalovirus, Human immunodeficiency virus, Simian immunodeficiency virus, Hepatitis A virus, Hepatitis B virus, Hepatitis C virus, Human papillomavirus, Poliovirus, rotavirus, caliciviruses, Measles virus, Mumps virus, Rubella virus, adenovirus, rabies virus, canine distemper virus, rinderpest virus, avian pneumovirus (formerly turkey rhinotracheitis virus), Hendra virus, Nipah virus, coronavirus, parvovirus, infectious rhinotracheitis viruses, feline leukemia virus, feline infectious peritonitis virus, avian infectious bursal disease virus, Newcastle disease virus, Marek's disease virus, porcine respiratory and reproductive syndrome virus, equine arteritis virus and various Encephalitis viruses.

The compositions of this invention are useful in enhancing response against fungal pathogens such as *Aspergillis, Blastomyces, Candida, Coccidiodes, Cryptococcus* and *Histoplasma* or against parasites including *Leishmania major, Ascaris, Trichuris, Giardia, Schistosoma, Cryptosporidium, Trichomonas, Toxoplasma gondii* and *Pneumocystis carinii.*

Compositions of this invention may also be useful for the prevention and/or treatment of disease(s), without limitation, such as autoimmune disease, such as multiple sclerosis, lupus and rheumatoid arthritis and others, asthma, atherosclerosis, Alzheimer disease, amyloidosis or amyloidogenic disease, and cancers. Clotting disorders and other vascular injuries caused by other infections, injury, aging, thrombocytopenia, inappropriate thrombus formation, myelodysplasia, AML, and the like may also be treated according to the methods of this invention. These compositions and methods can be useful to treat allergic reactions to allergens such as pollen, insect venoms, animal dander, fungal spores and drugs (such as penicillin). Other conditions that are treated by the methods of this invention included disease characterized by unwanted thrombus formation, amyloid deposition, diabetes, and gastroesophageal reflux disease, among others. The methods of this invention may also be useful in the enhancement of wound healing. The selection of the disorder to be treated by the compositions and methods of this invention is not a limitation of this invention. One of skill in the art may readily include other disorders suitable for the treatment described herein.

One method for treating a disorder in a mammal according to this invention includes the step of delivering to a mammal a recombinant nucleic acid molecule comprising a first sequence comprising a transgene encoding a product under the control of regulatory sequences that direct expression of the product of the transgene in a hematopoietic stem cell, a progenitor cell of the hematopoietic lineage, or a cell differentiated therefrom. Depending upon the identity of the regulatory sequence and the transgene, the method permits a differentiated cell of a hematopoietic lineage to express the product of the selected transgene at a suitable site in the mammal. Where the differentiated cell is secretory, the cell may express the transgene produce ectopically and target the expression to a particular site. For example, a plasmid expressing a transgene will target to the site of vascular injury or thrombus formation.

In one embodiment, therefore, the method of the invention involves harvesting stem cells or progenitor cells from bone marrow of a patent, transferring the nucleic acid molecule into the cells ex vivo and reinfusing the cells into the bone marrow or peripheral blood of the mammalian patient. Alternatively, the method of treatment can involve infusing or injecting into the patients bone marrow or blood a non-self transfected host cell.

In another embodiment, the method of the invention involves harvesting differentiated cells of the hematopoietic lineage from peripheral blood of a mammalian patient; transferring the nucleic acid molecule into the differentiated cells; and returning these cells into the blood of the patient. Alternatively, the method of treatment can involve infusing or injecting into the patients blood a non-self transfected differentiated host cell.

In still another embodiment of this invention, a method of treatment can involve directly administering to a mammalian patient, simply the nucleic acid molecule, i.e., as naked DNA. The regulatory sequences should aid in the uptake of the molecule by the appropriate differentiated cells of the hematopoietic lineage.

Thus, as one specific embodiment, the invention provides a method for enhancing coagulation in a patient by delivering to the mammalian patient with an insufficient clotting mechanism a recombinant nucleic acid molecule (or a platelet containing the molecule) comprising a first sequence comprising a transgene encoding a product under the control of regulatory sequences that direct expression of the product of the transgene in a platelet. Preferably the regulatory sequence would be a platelet-specific sequence mentioned above. Examples of suitable transgenes for this method are transgenes encoding one or more of Factor VIIa, Factor VIII, Factor IX or fibrinogen.

Another specific embodiment involves a method for preventing or reducing coagulation in a mammalian patient, where needed. According to this method, the patient is administered a recombinant nucleic acid molecule (or a platelet containing the molecule) comprising a first sequence comprising a transgene encoding a product under the control of regulatory sequences that direct expression of the product of the transgene in a platelet. Preferably the regulatory sequence would be a platelet-specific sequence mentioned above. Examples of suitable transgenes for this method are transgenes encoding one or more of urokinase plasminogen activator, plasminogen, tissue plasminogen activator, and tissue factor pathway inhibitor.

Another example of a method of this invention is a method for enhancing coagulation in a mammalian patient by delivering to the patient a recombinant nucleic acid molecule (or an erythrocyte containing the molecule) comprising a first sequence comprising a transgene encoding a product under the control of regulatory sequences that direct expression of the product of the transgene in an erythrocyte. Preferably the regulatory sequence would be an erythrocyte-specific sequence mentioned above. Examples of suitable transgenes for this method are transgenes encoding a urokinase plasminogen activator receptor, preferably expressed on the cell surface.

Still another example of this invention is a method for treating acute lung injury and sepsis in a mammalian patient. This method includes delivering to the patient a recombinant nucleic acid molecule (or neutrophils containing the molecule) comprising a first sequence comprising a transgene encoding a product under the control of regulatory sequences that direct expression of the product of the transgene in a neutrophil. Preferably the regulatory sequence would be a neutrophil-specific sequence mentioned above. Examples of a suitable transgene for this method is a transgene encoding activated Protein C.

The methods and compositions of this invention may also be employed in a method for treating parasitic helminth infection of a mammalian human or non-human patient. This method involves delivering to a mammal a recombinant nucleic acid molecule (or eosinophils containing the molecule) comprising a first sequence comprising a transgene encoding a product under the control of regulatory sequences that direct expression of the product of the transgene in eosinophils. Preferably the regulatory sequence would be an eosinophil-specific sequence mentioned above. Examples of a suitable transgene for this method is a transgene encoding a protein toxic to a helminth.

Another method according to this invention involves treating asthma or allergic responses in a mammalian patient. This method involves delivering to a mammal a recombinant nucleic acid molecule (or an eosinophils containing same) comprising a first sequence comprising a transgene encoding a product under the control of regulatory sequences that direct expression of the product of the transgene in an eosinophil. Preferably the regulatory sequence would be an eosinophil-specific sequence mentioned above. Examples of a suitable transgene for this method are transgenes encoding one or more of human TSG6, an antibody to IL-1 receptor alpha, and an anti-inflammatory protein.

The invention also includes a method for treating a viral infection in a mammal comprising delivering to a mammal a recombinant nucleic acid molecule (or NK cell containing same) comprising a first sequence comprising a transgene encoding a product under the control of regulatory sequences that direct expression of the product of the transgene in a natural killer cell. Preferably the regulatory sequence would be an NK cell-specific sequence mentioned above. Examples of a suitable transgene for this method is a transgene encoding a neutralizing antibody against a viral coat protein, e.g., anti-HIV gag protein, anti-HPV proteins, anti-HIV proteins, etc.

Finally, as demonstrated specifically by the examples below, the present invention provides a method for the treatment and prevention of undesirable thrombus development in a mammalian patient by administering to the patient a recombinant nucleic acid molecule (or platelet containing same) comprising a first sequence comprising a transgene encoding a product under the control of regulatory sequences that direct expression of the product of the transgene in a platelet. As illustrated below, a platelet that ectopically expressed u-PA under the control of the platelet specific PF4 promoter was able to control thrombus formation in a patient. See the Examples below.

The nucleic acid molecules or host cells are employed in compositions containing an physiologically acceptable diluent or a pharmaceutically acceptable carrier, such as sterile water or sterile isotonic saline. The compositions may also be mixed with such diluents or carriers in a conventional manner. As used herein the language "pharmaceutically acceptable carrier" is intended to include any and all solvents, dispersion media, coatings, antibacterial and antifungal agents, isotonic and absorption delaying agents, and the like, compatible with administration to humans or other vertebrate hosts. The appropriate carrier will be evident to those skilled in the art and will depend in large part upon the route of administration.

The compositions may also include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition. Other formulations may optionally include a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Still additional components that are present are adjuvants, preservatives, chemical stabilizers, or other proteins. Typically, stabilizers, adjuvants, and preservatives are optimized to determine the best formulation for efficacy in the target human or animal. Suitable exemplary preservatives include chlorobutanol, potassium sorbate, sorbic acid, sulfur dioxide, propyl gallate, the parabens, ethyl vanillin, glycerin, phenol, and parachlorophenol. Suitable stabilizing ingredients that are used include, for example, casamino acids, sucrose, gelatin, phenol red, N-Z amine, monopotassium diphosphate, lactose, lactalbumin hydrolysate, and dried milk.

Various cytokines and lymphokines are also suitable for inclusion in the compositions of this invention or administration therewith. One such cytokine is granulocyte-macrophage colony stimulating factor (GM-CSF), which has a nucleotide sequence as described in U.S. Pat. No. 5,078,996, which is hereby incorporated by reference. A plasmid containing GM-CSF cDNA has been transformed into E. coli and has been deposited with the American Type Culture Collection (ATCC), 10801 University Boulevard, Manassas, Va. 20110-2209, under Accession Number 39900. The cytokine Interleukin-12 (IL-12) is described in U.S. Pat. No. 5,723,127, which is hereby incorporated by reference (available from Genetics Institute, Inc., Cambridge, Mass.). Other cytokines or lymphokines include but are not limited to, the interleukins 1-α, 1-β, through 24, the interferons-α, β and γ, granulocyte colony stimulating factor, and the tumor necrosis factors α and β.

Still other suitable optional components of the compositions of this invention include, but are not limited to: surface active substances (e.g., hexadecylamine, octadecylamine, octadecyl amino acid esters, lysolecithin, dimethyl-dioctadecylammonium bromide), methoxyhexadecylgylcerol, and pluronic polyols; polyamines, e.g., pyran, dextransulfate, poly IC, carbopol; peptides, e.g., muramyl dipeptide, dimethylglycine, tuftsin; oil emulsions; and mineral gels, e.g., aluminum phosphate, etc. and immune stimulating complexes, liposomes, polysaccharides, lipopolysaccharides and/or other polymers.

In addition to a carrier as described above, compositions composed of polynucleotide molecules desirably contain optional polynucleotide facilitating agents or "co-agents", such as a local anesthetic, a peptide, a lipid including cationic lipids, a liposome or lipidic particle, a polycation such as polylysine, a branched, three-dimensional polycation such as a dendrimer, a carbohydrate, a cationic amphiphile, a detergent, a benzylammonium surfactant, or another compound that facilitates polynucleotide transfer to cells. Such a facilitating agent includes bupivacaine (see U.S. Pat. No. 5,593,972, which is hereby incorporated by reference). Other non-exclusive examples of such facilitating agents or co-agents useful in this invention are described in U.S. Pat. Nos. 5,703,055; 5,739,118; 5,837,533; International Patent Publication No. WO96/10038, published Apr. 4, 1996; and International Patent Publication No WO94/16737, published Aug. 8, 1994, which are each incorporated herein by reference.

Most preferably, the local anesthetic is present in an amount that forms one or more complexes with the nucleic acid molecules. When the local anesthetic is mixed with nucleic acid molecules or plasmids of this invention, it forms a variety of small complexes or particles that pack the DNA and are homogeneous. Thus, in one embodiment of the compositions of this invention, the complexes are formed by mixing the local anesthetic and at least one plasmid of this invention. Any single complex resulting from this mixture may contain a variety of combinations of the different plasmids. Alternatively, in another embodiment of the compositions of this invention, the local anesthetic is pre-mixed with each plasmid separately, and then the separate mixtures combined in a single composition to ensure the desired ratio of the plasmids is present in a single composition, if all plasmids are to be administered in a single bolus administration. Alternatively, the local anesthetic and each plasmid are mixed separately and administered separately to obtain the desired ratio. When the facilitating agent used is a local anesthetic, preferably bupivacaine, an amount of from about 0.1 weight percent to about 1.0 weight percent based on the total weight of the polynucleotide composition is preferred. See, also, International Patent Publication No. WO99/21591, which is hereby incorporated by reference, and which teaches the incorporation of benzylammonium surfactants as co-agents, preferably administered in an amount of between about 0.001-0.03 weight %. According to the present invention, the amount of local anesthetic is present in a ratio to the nucleic acid molecules of 0.01-2.5% w/v local anesthetic to 1-10 µg/ml nucleic acid. Another such range is 0.05-1.25% w/v local anesthetic to 100 µg/ml to 1 ml/ml nucleic acid.

As used, such a polynucleotide composition may express the transgene product on a transient basis in vivo; no genetic material is inserted or integrated into the chromosomes of the host.

The compositions may also contain other additives suitable for the selected mode of administration of the composition. The composition of the invention may also involve lyophilized polynucleotides, which can be used with other pharmaceutically acceptable excipients for developing powder, liquid or suspension dosage forms. See, e.g., Remington: The Science and Practice of Pharmacy, Vol. 2, 19$^{th}$ edition (1995), e.g., Chapter 95 Aerosols; and International Patent Publication No. WO99/45966, the teachings of which are hereby incorporated by reference. Routes of administration for these compositions are combined, if desired, or adjusted.

These nucleic acid molecule-containing compositions can contain additives suitable for administration via any conventional route of administration. In some embodiments, administration is intravenous or directly into the bone marrow. In some embodiments, the composition of the invention is prepared for administration to human subjects in the form of, for example, liquids, powders, aerosols, tablets, etc.

The compositions of the present invention (whether host cell-containing or nucleic acid molecule-containing compositions), as described above, are not limited by the selection of the conventional, physiologically acceptable, carriers, adjuvants, or other ingredients useful in pharmaceutical preparations of the types described above. The preparation of these pharmaceutically acceptable compositions, from the above-described components, having appropriate pH isotonicity, stability and other conventional characteristics is within the skill of the art.

Suitable routes of administration include, but are not limited to, intranasal, oral, vaginal, rectal, parenteral, intradermal, transdermal, intramuscular, intraperitoneal, subcutaneous, intravenous and intraarterial. The appropriate route is selected depending on the nature of the composition used, and an evaluation of the age, weight, sex and general health of the patient and the components present in the immunogenic composition, and similar factors by an attending physician.

Similarly, suitable doses of compositions of this invention are readily determined by one of skill in the art, depending upon the condition being treated, the health, age and weight of the veterinary or human patient, and other related factors, and the other characteristics of the composition, e.g., nucleotide molecule, vector or host cell. In general, selection of the appropriate "effective amount" or dosage for the composition(s) of the present invention will also be based upon the form of the composition, the identity of the transgene and host cell, as well as the physical condition of the subject. The method and routes of administration and the presence of additional components in the compositions may also affect the dosages and amounts of the compositions. Such selection and upward or downward adjustment of the effective dose is within the skill of the art. The amount of composition required to produce a suitable response in the patient without significant adverse side effects varies depending upon these factors. Suitable doses are readily determined by persons skilled in the art.

For example, the amounts of nucleotide molecules in the DNA and vector compositions are selected and adjusted by one of skill in the art. In one embodiment, each dose will comprise between about 50 µg to about 1 mg of nucleic acid molecule, e.g., DNA plasmid, per mL of a sterile solution. Generally, a suitable dose where the vector is a viral vector is in the range of $10^3$ to $10^{18}$, preferably about $10^5$ to $10^{16}$ transducing units (TU) per dose, and most preferably, about $10^7$ to $10^9$ TU for an adult human having a weight of about 80 kg. Transducing Units (TU) represents the number of infectious particles and is determined by evaluation of transgene expression upon infection of host cells. Generally, when used for ex vivo therapy, the host cells are infected with $10^5$ TU to $10^{10}$ TU viral vectors for each $10^1$ to $10^{10}$ cells in a population. However, other suitable ex vivo dosing levels are readily selected by one of skill in the art. This dose is formulated in a pharmaceutical composition, as described above (e.g., suspended in about 0.01 mL to about 1 mL of a physiologically compatible carrier) and delivered by any suitable means.

The number of doses and the dosage regimen for the composition are also readily determined by persons skilled in the art. The intended therapeutic or prophylactic effect is conferred by a single dose of the composition or may require the administration of several doses, in addition to booster doses at later times. The dose is repeated, as needed or desired, daily, weekly, monthly, or at other selected intervals.

V. EXAMPLES OF THE INVENTION

As illustrated in the examples below, the methods of this invention were employed to modify the biological behavior of platelets by causing these hematopoietic lineage cells to ectopically express a protein of interest at a site of vascular injury.

A. Transgenic Animal Model

A murine urokinase-type plasminogen activator (u-PA) transgene was expressed transgenically in mice under the regulatory control of a platelet factor 4 promoter that directed expression to platelets. The resultant transgenic animals have altered platelet biology; i.e., they express and store u-PA selectively in their platelet alpha-granules, in the absence of systemic fibrinolysis and bleeding characteristic of transgenic over-expression of u-PA in the liver (Heckel, J. L. et al, 1990 *Cell* 62:447-456). These transgenic mice also had a characteristic bleeding diathesis similar to that seen in patients with Quebec Platelet Disorder (QPD) that is predominantly at the time of parturition and that can be controlled by tranexamic acid.

More importantly, these mice were resistant to the development of occlusive carotid arterial thrombi in the absence of systemic fibrinolysis. The mice rapidly lysed pulmonary venous thrombi or emboli. Moreover, transfusion of small numbers of urokinase-expressing platelets into wildtype recipients prevented formation of stable, occlusive carotid arterial thrombi.

Thus, this animal model confirms that ectopic expression of u-PA in platelets is the etiology of inherited QPD, provides new insights into the contribution of activated platelets to thrombus stability, and provides a new method for preventing inopportune thrombus development. The transgenic model shows that developing megakaryocytes are genetically altered in such a way that platelet function is effectively tipped from pro-thrombotic to anti-thrombotic. These examples provide a evidence that ectopic u-PA expression in platelets can be achieved.

B. Summary Of The Examples

The present invention involves the discovery that ectopic expression of proteins in platelets are useful to favorably alter the hemostatic balance at sites of thrombosis. Fibrinolytic agents can be delivered to sites of incipient thrombus formation through selective storage in platelets, a new method to prevent thrombosis and hemorrhage. As demonstrated in the Examples below, ectopically expressed proteins carrying a signal peptide are stored within platelets and released specifically at sites of injury. By use of this method, one may alter the prothrombotic role of platelets as a means to modify pathological thrombus development.

The method of this invention has clinical application in situations where re-thrombosis or the prevention of extension of a previous thrombosis is desirable for an extended period of time. For example, transient expression of u-PA in megakaryocyte progenitors harvested from peripheral blood and treated with present-day retroviral gene-transfer vectors are a potent mechanism to prevent post-angioplasty restenosis for several weeks to months with low risk of long-term alteration of the recipient's stem cell genome. Untoward bleeding associated with the therapy can be controlled by treatment with an anti-fibrinolytic agent such as tranexamic acid. Lastly, the methods of this invention enables delivery of pro-hemostatic proteins to sites of vascular interruption in patients with diverse hemorrhagic disorders.

To determine whether developing megakaryocytes could be altered to express either anti-thrombotic or pro-hemostatic proteins, which would be stored in platelet and be released in a concentrated fashion directly at a site of injury, a transgenic model was developed. In this model, the expression of u-PA was directed to platelets of transgenic mice using the PF4 promoter, which is known to drive megakaryocyte-specific expression (Ravid, K. et al, 1991 *Proc. Nat. Acad. Sci. U. S. A.* 88:1521-1525). It was found that platelet u-PA was stored in platelets and was released within developing thrombi when platelets were activated. The u-PA was partially counter-balanced by PAI-1, which is present in platelet alpha-granules of both human and mice platelets (Ngo, T. H., and Declerck, P. J. 1999 *Thromb. Haemost.* 82:1510-1515). This method tipped the balance sufficiently to lessen the resistance of clots, especially in the arterial circulation where platelet activation is more intense, to commonly employed agents.

The "line #19" transgenic animals, described in the examples below, had u-PA mRNA, u-PA-like protease activity and u-PA protein detectable in their platelets. Several of the constituent platelet alpha-granular proteins, including vWF and fibrinogen, were partially degraded, probably due to plasmin-mediated proteolysis. However, unlike the previously described murine u-PA over-expressors driven by a liver-specific promoter (Heckel, J. L. et al, cited above), these animals did not demonstrate systemic fibrinolysis. Few of the transgenic adults developed spontaneous hemorrhage despite life-long expression of elevated levels of platelet-uPA. The platelet counts were normal, and the red cells had normal morphology. Plasma fibrinogen was intact and D-dimers were not detected in the plasma of these mice.

Megakaryocyte-expressed u-PA was not secreted to a considerable extent, but rather was preferentially stored in the circulating platelets, where it led to the digestion of alpha-granular proteins, as in the human disorder termed QPD. The u-PA within the alpha-granules was predominantly in the form of enzymatically active tcu-PA, as determined by immunoblotting. Platelets are believed to endocytose sufficient plasminogen from plasma (Holt, J. C., and Niewiarowski, S. cited above) into their alpha-granules to form plasmin, as suggested by the capacity of u-PA platelets to digest exogenously added Factor V. Plasmin formation is initiated by the low level of intrinsic activity of scu-PA (Lenich, C. et al, 1997 *Blood* 90:3579-3586) or by the activation of scu-PA by u-PAR (Higazi, A. et al, 1995 *J. Biol. Chem.* 270:17375-17380) or, less likely, by another platelet granular enzyme. It is likely that plasmin, once formed, then converts additional scu-PA to tcu-PA within the granules themselves, although the role of other proteases again cannot be excluded. Little tcu-PA was found as high molecular weight complexes with PAI-1. Murine platelets may contain less PAI-1 than human platelets, or the latent state of PAI-1 within the granules (Booth, N. A. et al, 1988 *Brit. J. Haematol.* 70:327-333; Lang, I. M. et al, 1992 *Blood* 80:2269-2274) may limit its binding to u-PA, or complex formation is inhibited by u-PAR (Higazi, A. A.-R et al, 1996 *Blood* 87:3545-3549), the pH or other components of the alpha-granules, or, more likely, most of the PAI-1 was degraded by the u-PA.

Aside from peripartum deaths, adult transgenic mice had few spontaneous mucosal bleeding episodes, had normal bleeding times, and exhibited normal platelet aggregation in vitro. However, these animals clearly were resistant to developing occlusive thrombi in a ferric chloride-induced carotid artery thrombosis model. Only 5% of the u-PA expressing animals developed complete arterial occlusion by the end of the study (60 minutes) as opposed to 85% of their wildtype littermates (Table 1). It appears that the thrombi that did form were far more friable and transitory in nature. Moreover, lysis of preformed, fibrin microemboli targeted to the lungs occurred far more rapidly in the u-PA expressing mice than in their wildtype counterparts. These data suggest that platelet activation initiated by fibrin contributes to thrombus growth or stability on the venous side of the circulation (Bdeir, K. et al, cited above) and that local release of u-PA causes rapid lysis of the nascent thrombi.

Recent studies using combined platelet glycoprotein IIb/IIIa inhibitors and agents (Murciano, J. C. et al, 2002 *Am. J. Physiol. Lung Cell. Mol. Physiol.* 282:L529-539), and studies using pharmacological inhibition of PAI-1 (Rupin, A. et al, 2001 *Thromb. Haemost.* 86:1528-1531) are consistent with these conclusions.

Transfusion of u-PA platelets equivalent to 10% of the recipient's platelet mass potently inhibited thrombus development in wildtype recipients. The ability of the transgenic platelets to disrupt thrombus development is more likely to be due to the released u-PA than to degradation of hemostatic alpha-granular proteins for several reasons. First, the near total loss of granular proteins, as in the Gray Platelet Disorder, is associated with little or no bleeding (Rao, A. K, 1998 *Am. J. Med. Sci.* 316:69-76, 1998). Second, arterial thrombi are enriched with PAI-1. The absence of PAI-1 in mice results in a failure of thrombus formation in a chemically-induced carotid artery thrombosis model (Eitzman, D. T. et al, 2000 *Blood* 95:577-580). Third, transfusion of transgenic platelets into wildtype recipients that had been drinking water containing tranexamic acid reversed the effect of platelet-associated u-PA on thrombus formation (Table 2), notwithstanding the persistence of degraded alpha-granular proteins in the transfused platelets. These results suggest that it is the u-PA that is the major cause for the defective hemostasis in these mice, although a contribution from degraded alpha-granular proteins is by no means excluded.

Based on an analysis of the data generated by these examples similar to that of (Kahr, W. H. et al., cited above), line #19 platelets were estimated to contain ~20 pg of u-PA per μg of total platelet protein. Moreover, there are striking similarities between the phenotype of the QPD patients and these transgenic mice. This provides additional support for the conclusion that this syndrome results from the ectopic expression of u-PA in platelets. Both are dominantly inherited disorders. Both QPD and the transgenic mice ectopically express u-PA in the platelets, which also contain many degraded alpha-granular proteins. In both QPD and the transgenic mice, the ectopic expression of u-PA is essentially confined to the platelets, and insufficient u-PA is secreted into the plasma to cause disseminated fibrinolysis. The phenotype of neither is improved by platelet infusions, but is improved by use of an anti-fibrinolytic agent, such as tranexamic acid.

In summary, these studies support the etiology of QPD as being due to ectopic expression of u-PA in platelets. Second, they highlight the importance of the balance between platelet-dependent coagulation and fibrinolysis during thrombus growth on venous as well as on the arterial side of the circulation. Third, they show that the ectopic expression of u-PA in platelets is a valid method for preventing untoward thrombus development.

The following examples are provided to illustrate construction and use of the recombinant vectors and compositions of the invention and do not limit the scope thereof. One skilled in the art will appreciate that although specific elements, reagents and conditions are outlined in the following examples, modifications can be made which are meant to be encompassed by the spirit and scope of the invention.

Example 1

Establishment of Transgenic Mice Expressing U-PA Message

A transgene was designed as illustrated schematically in FIG. 1. 1.2 kb of the 129 SV murine platelet factor 4 (PF4) proximal promoter region plus its 5'-untranslated region (UTR) (Zhang, C. et al, 2001 *Blood* 98:610-607) was PCR amplified with an artificial upstream Xba I site and a downstream Kpn I site added. The inventors found that this promoter could also drive megakaryocyte-specific expression of LacZ in transgenic mice (data not shown). This promoter was inserted in place of the albumin enhancer/promoter immediately upstream of a mouse u-PA minigene construct that contained a 3'-UTR and poly-adenylation sequence from the human growth hormone (hGH) gene. This construct was previously described in Heckel, J. L. et al, 1990 *Cell* 62:447-456, which is incorporated by reference herein.

A 10.2 kb Sac II fragment containing this construct was used to create transgenic mice by pronuclear injections following standard methods at the University of Pennsylvania Transgenic Mice Core Facility. Seven transgenic founders were obtained with copy numbers ranging from 1 to >20 copy per haploid genome.

Genomic DNA was isolated from mouse tails using a QIAamp™ DNA Mini Kit (Qiagen, Valencia, Calif.). Positive founder lines were detected by genomic Southern blot analysis (Tunnacliffe, A. et al, 1992 *Blood* 79: 2896-2900). Genomic Southern blot analysis was made of Bgl II-digested DNA from a wildtype animal and the three lines that had offspring with the fewest copy numbers of the transgene (Lines #13, #19 and #49). After digestion, genomic DNA was separated on a 1% (wt/vol) agarose gel. The probe used was the mouse PF4 proximal promoter from −680 to −360 bp upstream of the transcriptional start site (Zhang, C. et al, cited above), and the final probed membrane was exposed on a PhosphorImaging screen (Amersham Biosciences, Sunnyvale, Calif.). The 2.8 kb Bgl II fragment was detected for the transgene in the genomic Southern blot.

The transgene copy number per haploid genome was determined by phosphorimaging (not shown). The intensity of bands on film was analyzed using the Imagequant PhosphorImager software (Amersham Biosciences). The copy number was determined by comparing the intensity of the 2.8 kb transgene PF4 band to the native genomic 1.2 kb PF4 band.

Three male founders had offspring with the fewest copy number of transgene (i.e., line #13, copy number 1, line #19, copy number 2 and line #49, copy number 3), although the line #49 transgene did not transmit well (see below), and these mice were not available for most studies. All three female founders had high transgene copy number, and when pregnant, died peripartum from uterine hemorrhage (see below). The final male founder was high copy number (>20) and never produced offspring.

Founder animals and their offspring were also characterized by genomic PCR analysis using a mouse PF4 5'-UTR (5'-CACTTAAGAGCCCTAGACCCATTTCC-3'; SEQ ID NO: 1) sense primer and a mouse u-PA exon 2 (5'-TTCA- GAGTTTTTCACCACCAA-3'; SEQ ID NO: 2) antisense primer, which generates a 479 bp genomic and a 114 bp cDNA band. RT-PCR analysis of total platelet RNA was performed on lines #13, #19 and #49 for the 114 bp transgenic u-PA message that extended from the 5'-UTR of PF4 into the murine u-PA $2^{nd}$ exon in their platelets. The 185 bp PF4 message was used as a positive control of the platelet nature of the RNA. PCR was performed to confirm founder lines using primers complementary to the mouse PF4 5'-UTR and exon 2 of the murine u-PA gene (data not shown).

Direct sequence analysis of this RT-PCR product for all three lines confirmed that the $1^{st}$ intron was appropriately spliced out (data not shown). When RT-PCR was performed on multiple tissues, e.g., spleen, liver, lung, heart, kidney, adrenal, tongue, brain, and bone marrow, only bone marrow tested positive for the 114 bp transgenic-derived u-PA mRNA band. All samples showed the 249 bp HPRT positive control cDNA band. Immunohistochemistry of the bone marrow showed detectable u-PA only in morphologically recognizable megakaryocytes in the transgenic animals, but not in wild-type marrow.

All biological studies described below were done with transgenic animals that had been backcrossed at least 4 generations onto a C57BL6 background. Wildtype littermates served as controls. Cardiac or portal vein blood was drawn from mice into $\frac{1}{10}^{th}$ volume of 3.8% sodium citrate. All studies were approved by the Animal Care and Use Committee of the Children's Hospital of Philadelphia.

Example 2

Transgenic U-PA Message Detection

The animals of Example 1 were then examined to determine whether they expressed u-PA in their platelets. Murine platelet RNA was isolated using RNA STAT-60™ (Tel-Test, Friendswood, Tex.) as previously described (Zhang, C. et al, cited above). Tissues (~100 mg each) from these animals were collected, rinsed vigorously with saline, disaggregated in 500 µl of RNA STAT-60™, and RNA was isolated (Zhang, C. et al, cited above). Some platelet RNA samples were pretreated with DNase free RNase (1 U/10 µl reaction, Sigma, St. Louis, Mo.) or RNase free DNase (1 U/10 µl reaction, Life Technologies, Gaithersburg, Md.) for 1 hour at 37° C.

Reverse transcription was performed using the SuperScript II Reverse Transcriptase Kit™ (Life Technologies) as per the manufacturer's instructions. PCR amplification of the transgenic u-PA cDNA was accomplished using the two primers discussed above. Platelet-specific control RT-PCR primers for PF4 message were sense 5'-AATTCTCGG-GATCTGGGT-3' SEQ ID NO: 3 and antisense 5'-CTGGGCTCTAGACAGCAGT-3 SEQ ID NO: 4 (Eisman, R. et al, 1990 Blood 76:336-344), with an expected cDNA product of 185 bp. RT-PCR for the housekeeping gene human phosphoribosyltransferase (HPRT) used primers 5'-GCTG-GTGAAAAGGACCT CT-3' SEQ ID NO: 5 and 5'-CACAG-GACTAGAACACCTGC-3' SEQ ID NO: 6, with an expected cDNA product of 249 bp (Jackson, C. L. et al, 1984 Proc. Nat. Acad. Sci. U.S.A. 81:2945-2949).

Platelet murine transgenic u-PA cDNA band was isolated using a QIAkwik™ Gel Extraction Kit (Qiagen) and directly sequenced using an ABI 373A automated sequencer (ABI Instruments, Foster City, Calif.).

Example 3

Immunogistochemical Staining for Murine Urokinase

Spleen and bone marrow aspirates from wildtype and murine u-PA transgenic mice were stained for murine u-PA expression using a mouse monoclonal anti-murine u-PA antibody (A10, Molecular Innovations, Inc., Southfield, Mich.) as the primary antibody and a biotinylated anti-mouse immunoglobulin (ARK detections system, DAKO, Caprinteria, Calif.) as the secondary antibody. Specifically, formalin-fixed, paraffin-embedded 5 µm sections were deparaffinized in xylene and rehydrated. Endogenous peroxidase activity was quenched with 0.9% peroxide in methanol for a total of 20 minutes. Slides were then treated with trypsin (1 mg/ml in PBS) for 10 minutes at 37° C. After incubation of the monoclonal anti-murine u-PA antibody (0.5 µg/ml) with biotinylated ARK reagent (according to manufacturer's instructions) for 15 minutes at room temperature, the slides were stained at room temperature for 2 hours. Slides were washed and incubated with Streptavidin-HRP (DAKO) for 15 minutes at room temperature. Slides were again washed DAB reagent (DAKO) was applied for 5 minutes at room temperature. Slides were counterstained with dilute (1:10) hematoxylin for 30 seconds.

Immunohistochemistry of the bone marrow in wildtype and line #19 mice showed detectable u-PA only in morphologically recognizable megakaryocytes in the transgenic animals, but not in wildtype marrow.

Example 4

U-PA Activity in the Platelets

Zymogram and Immunoblot Studies

A. Zymogram Studies

Platelet-rich plasma (PRP) was obtained as described in Zhang, cited above. Platelet counts were determined using a HemaVet counter (Triad Associates, Concord, Calif.). The platelets were pelleted at 800 g for 5 minutes and resuspended immediately in 1× NuPage Sample Buffer (Invitrogen, Carlsbad, Calif.). Total platelet protein and platelet releasates (0.5 to 10 µg/lane) were separated by size under non-reducing conditions on a 12% SDS-polyacrylamide gel (SDS-PAGE) with 0.4% nonfat dry milk, e.g., casein (Carnation Instant Skim Milk Powder, Nestle, Fulton, N.Y.) with or without supplemental 20 µg/ml human plasminogen (American Diagnostica, Greenwich, Conn.), and then renatured with 0.5% Triton X-100 in PBS, pH 7.4, for 1 hour as previously described (Heckel, J. L. et al, cited above). The gel was incubated at 37° C. for 3 hours. A control lane of 0.1 ng of human 2-chain urokinase (American Diagnostica) was included in each gel.

Zymograms of two separate preparations of lysates from line #19 and #13 platelets and wildtype platelets (10 µg/lane) reveal a prominent band likely representing tcu- at ~45 kDa was seen with platelets from line #19 (data not shown). This is similar to what has been previously described for murine u-PA (Heckel, J. L. et al, cited above), consistent with the fact that mouse u-PA is not glycosylated. Line #13 and wildtype lanes had no detectable zones of lysis, although twice as much platelet protein was loaded compared to the #19 line lanes. Omission of plasminogen from the zymogram or the inclusion of the selective u-PA inhibitor amiloride in the zymogram (data not shown) abolished lysis induced by transgenic platelet lysates and the human tcu-PA control. These results are similar to those reported for QPD platelets, although the lower band in the human disorder was ~10% as intense as the upper band, rather than ~30% as seen in lysates from the transgenic mouse platelets.

B. Immunoblots

To confirm the presence of u-PA in the transgenic platelets, total platelet proteins were separated by size on a non-reducing Western gel and then immunoblotted with A10, an anti-murine u-PA mAb. Platelet immunoblots were performed as previously described (Zhang, C. et al, cited above), except that 4-8% gradient gels were used (NuPAGE Novex Bis-Tris Gels, Invitrogen, Carlsbad, Calif.). Gels were run under non-reducing conditions, except when studying platelet fibrinogen, where 1 µl of reducing agent (NuPAGE Sample Reducing Agent) was added per sample. Mouse u-PA was detected with a murine anti-mouse u-PA monoclonal antibody (A10, Molecular Innovations, Southfield, Mich.) added at a 1:75 dilution and detected with a biotinylated anti-mouse monoclonal antibody (Molecular Innovations) followed by peroxidase-conjugated streptavidin (StreptABComplex/HRP, DAKO, Carpinteria, Calif.). Murine vWF was detected using a 1:200 dilution of a horse radish peroxidase (HRP)-conjugated rabbit anti-human vWF polyclonal antibody (DAKO), and murine fibrinogen was detected using a 1:100 dilution of an HRP-conjugated goat anti-human fibrinogen polyclonal antibody (Rockland Immunochemicals, Gilbertsville, Pa.).

The Western blot of platelet lysates (10 µg/lane) for lines #19 and #13, wildtype, and renal extract (30 µg/lane) revealed a major doublet at ~45 kDa in line #19; total platelet lysate that was not seen in wildtype littermate platelet lysate (data not shown). The major component in the doublet appears to be tcu-PA and co-migrates with the renal extract control. The higher, less intense band is likely to be single chain uPA (scu-PA) or an otherwise modified tcu-PA as previously described (Franco, P. et al, 1997 *J. Cell Biol.* 137:779-791) and migrates similar to a band in renal extract. Thus, as with QPD platelet lysates, the major form of u-PA in the transgenic platelets appears to be tcu-PA (Kahr, W. H. et al., cited above).

Also, as with QPD platelet lysates, a few high molecular weight species were observed that likely include covalent complexes between PAI-1 and both tcu-PA and low molecular weight proteolytic derivatives of u-PA (Jiang, Y et al. 1996 *Blood* 87:2775-2781). The typical low molecular weight u-PA species commonly observed in biological specimens (~30 kD), was not a feature of platelet lysates. Rather, as observed with QPD platelets, a somewhat smaller low molecular weight u-PA species was observed in transgenic mouse platelet lysates. None of these mouse u-PA bands was detected when a comparable amount of platelet lysate from wildtype and line #13 mice were studied. This lack of detectable u-PA in Line #13 is consistent with the lack of u-PA activity seen in the above-described zymogram and in the clinical course of these animals (discussed below).

Example 5

Alpha-Granular Proteins

Several alpha-granular proteins, including vWF, fibrinogen and Factor V undergo proteolysis in QPD platelets. Proteolysis of these proteins has been attributed to the ectopically expressed u-PA (Kahr, W. H. et al., cited above). To determine whether the presence of mouse u-PA in platelets led to a similar expression of proteolytic activity and study the in vitro digestion of Factor V by platelet lysate, 10 ng of plasma-derived human Factor V (Rodney Camire, Children's Hospital of Philadelphia) was digested with either human tcu-PA (10 pg, American Diagnostica) or with 2.5 µg of total murine platelet lysate prepared from $1.3 \times 10^6$/µl platelets in the presence or absence of supplemental plasminogen (1 µg). The resultant digest was then separated by SDS-PAGE. Factor V was detected using a 1:100 dilution of an HRP-conjugated sheep anti-human Factor V polyclonal antibody (Affinity Biologicals, Inc., Hamilton, ON, Canada) as the primary antibody.

In a Western blot of platelet lysate (2.5 µg/lane) from lines #13 and #19 and wildtype mice immunoblotted with a rabbit anti-human vWF polyclonal antibody (not shown), vWF underwent extensive digestion in the line #19 platelets, compared with the intact high molecular weight vWF observed in the littermate wildtype sample. Platelet fibrinogen immunoblots of line #19 lysate consistently contained high molecular weight complexes that entered the gel poorly. These high molecular weight complexes are absent on a reduced gel, suggesting that they represent disulfide bond, cross-linked fibrinogen-derived products generated by u-PA. Consistent with the immunoblot for mouse u-PA, no degradation of vWF was seen in platelets from line #13 mice.

In a Western blot of reduced gel of platelet lysates as above or plasma (3 µg/lane for mouse and 6 µg/lane for human) proteins (not shown) both murine and human fibrinogen were detected using a goat anti-human fibrinogen polyclonal antibody. Platelet alpha-granular fibrinogen was also degraded in transgenic line #19, but not in line #13 and in wildtype platelets, as assessed on the non-reducing SDS-PAGE gel. In contrast, plasma fibrinogen was not degraded in line #19 mice.

This finding clearly contrasts with the systemic fibrinolysis that develops in the previously described u-PA over-expressing transgenic mice that were generated using a liver-specific promoter (Heckel, J. L. et al, cited above). Platelet fibrinogen immunoblots of line #19 lysate consistently contained high molecular weight complexes that entered the gel poorly. These high molecular weight complexes were absent on a reduced gel., suggesting that they represent disulfide-bonded, cross-linked, fibrinogen-derived products generated by u-PA and plasmin.

In another test to determine whether platelet releasate from the transgenic mice could proteolyze human Factor V in a manner similar to that seen in QPD, platelet lysate was incubated with human Factor V for up to 4 hours. Factor V (FV) (10 ng/lane) was digested with 2.5 µg/lane of the indicated platelet lysate or human u-PA (5 µg/lane) at room temperature, in the absence or presence of 100 µg/lane of plasminogen per lane.

Platelet lysate from line #19 digested the Factor V in a rapid fashion, with degradation nearly complete by 4 hours, giving a similar pattern to that seen with exogenously added human u-PA (data not shown). Platelets from wildtype littermates also degraded Factor V, but at a much slower rate. The addition of exogenous plasminogen to the platelet releasate enhanced Factor V digestion by line #19 platelet lysate, but had little effect on the rate of digestion by wildtype platelets. This suggests that the amount of plasminogen available in alpha-granules in the transgenic line #19 platelets is rate limiting for maximal protein degradation.

Example 6

Clinical Course and Hematologic Studies

A. Clinical Course

Fewer line #19 and #49 transgenic mice were born than expected. Assuming that 50% of the offspring from a cross between a hemizygous animal and a wildtype animal should be transgenic, line #19 showed a 68% mortality rate (57 transgenic animals vs. 175 wildtype littermates at weaning) and line #49 showed an 85% mortality rate (2 transgenic and 12 wildtype). Line #13 had a very low mortality rate, consistent with little platelet u-PA expression (71 transgenic and 80 wildtype). At day 16.5 of gestation, line #19 embryos looked normal and appeared at the expected frequency (10 transgenic and 11 wildtype), indicating that transgenic animals were lost peripartum. Surviving transgenic animals were normal for weight and growth, although occasional spontaneous deaths occurred among the adults secondary to subcutaneous or internal hemorrhage. Autopsies on two such adult line #19 mice expressing u-PA in their platelets showed examples of spontaneous hemorrhage: one mouse had free blood in the opened peritoneum and the other showed free blood filling a small intestinal loop.

However, when ten line #19 animals and ten littermate wildtype controls were specifically observed for >11 months, no deaths were observed in either group, suggesting a low rate of death in the line #19 animals.

As noted above, none of the female founder lines survived birthing. This was also true for pregnant line #19 and #43 transgenic females. In line #19, none of nine pregnant females survived giving birth, exsanguinating from uterine bleeding at birth (data not shown). Litter sizes were normal, with embryos containing equal numbers of wildtype and transgenic animals, and all embryos appeared normal in size (data not shown).

Three pregnant line #19 females were given tranexamic acid (20 mg/ml), an inhibitor of plasminogen activator, in their drinking water (Hattori, N. et al, 2000 *J. Clin. Invest.* 106:1341-50) during the last week of pregnancy and all survived. One lost her pups at birth, and the other two had small litters, consisting of 3 pups each (2 of the 6 were transgenic).

B. Blood Counts

Complete blood counts were performed on line #19 adult mice and wildtype littermate controls (n=10, each). Blood counts were measured using a Hemavet 850 (CDC Technologies, Inc, Oxford, Conn.) calibrated for murine blood. Dried blood smears were stained using Wright-Giemsa reagent (EM Science, Gibson, N.J.) and the red cell and platelet morphology was examined. Fibrin D-dimers were measured in plasma samples obtained according to manufacturer's instructions (Asserachrom D-Di, American Bioproducts Co., Diagnostica Stago, Asnieres, France).

Results of the counts showed nearly identical platelet counts and hemoglobin levels for the line #19 and wildtype controls (data not shown). Peripheral blood smears were normal, including normal platelet numbers and appearance and no evidence of red cell schistocytes or spherocytes (data not shown).

C. Platelet Aggregation

Platelet aggregation studies were performed as described previously (Kowalska, M. A. et al, 2000 *Blood* 96:50-57). Aggregation and dense granule ATP release were measured in a lumi-aggregometer (Chrono-Log, Havertown, Pa.). Agonists studied included collagen (1-5 µg/ml), ADP (1-5 µM), epinephrine (50 µM), and thrombin (0.1-1 U/ml) (Bachem Torrance, Calif.). Marrow samples from wildtype and transgenic mice were stained for mouse u-PA expression using the murine anti-mouse u-PA A10 primary antibody as described previously (Zhang, C. et al, cited above).

Platelet aggregation in response to collagen (1-5 µg/ml), ADP (1-5 µM), epinephrine (50 µM), and thrombin (0.1-1 U/ml) were also normal (data not shown). D-dimer measurements were negative in the line #19 mice (data not shown). Together with the measurements of plasma fibrinogen discussed above, these studies confirm that line #19 mice do not exhibit systemic fibrinolysis.

Example 7

Carotid Artery Thrombosis Model

Bleeding times were normal in line #19 mice when compared with wildtype littermate controls (5.8±3.2 mins versus 5.1±3.4 (n=7, each), respectively), but this test has previously proven to be an insensitive measurement of thrombotic tendency (Mayadas, T. N. et al, 1993 *Cell* 74:541-554). Therefore, the carotid artery injury thrombosis model was employed. This model has been used successfully to demonstrate a bleeding diathesis in diverse mouse backgrounds. This approach also permits study of the effect of ectopic expression of u-PA in platelets on thrombus development and stability.

Ferric chloride-induced arterial injury was performed according to published procedures (Fay, W. P. et al, 1994 cited above; Fay, W. P. et al, 1999 *Blood* 93:1825-1830) in 6-8 week old animals. Briefly, the right common carotid artery was exposed by blunt dissection, and a miniature Doppler flow probe (Model 0.5VB, Transonic Systems, Ithaca, N.Y.) was positioned around the artery. A 1×2 mm$^2$ strip of Number 1 Whatman filter paper (Fisher Scientific, Pittsburgh, Pa.) soaked in 10% ferric chloride was then applied to the adventitial surface of the artery for 2 min. The field was flushed with saline, and blood flow was continuously monitored for 30 minutes. The time to the initial complete occlusion and the presence or absence of arterial occlusion at 30 min was recorded.

To study the effects of a platelet transfusion, 1.2-1.5×10$^8$ gel-filtered platelets in 300 µl of gel-filtering buffer (4 mM NaH$_2$PO$_4$; 5 mM Hepes; 137 mM NaCl; 2.6 mM KCl; 5 mM glucose; 1 mM MgCl$_2$) was prepared as previously described (Kowalska, M. A. et al, cited above) and infused into the left jugular vein immediately before the ferric chloride patch was applied. Platelets were used within 2 hours of collection. Total blood counts were measured immediately before and 2 minutes after platelet infusion.

Unlike their wildtype littermates, few transgenic animals expressing platelet u-PA formed completely occlusive coronary artery thrombi after ferric chloride-induced injury (Table 1), and those that occluded tended to reopen rapidly. At 30 minutes, only 5% of occlusive thrombi formed in the u-PA mice remained as opposed to the >85% of thrombi formed in controls (Table 1). Supplementing the transgenic animals with 20 mg/ml tranexamic acid, a small molecule inhibitor of plasminogen activation, reversed this protection from occlusive coronary artery thrombosis. Line #13 mice occluded normally.

TABLE 1

Ferric chloride thrombosis model.

| Founder line | Time to initial occlusion (mins) | Initial occlusion (5) | Occluded at 30 mins (%) |
|---|---|---|---|
| WT | 8.8 ± 4.3 | 31/34 (91%) | 29/34 (85%) |
| #13 | 6.8 ± 3.3 | 9/10 (90%) | 9/10 (90%) |
| #19 | 10.3 ± 4.8 | 4/20 (20%)‡ | 1/20 (5%)‡ |
| WT + TA | 8.3 ± 1.1 | 5/5 (100%) | 4/5 (80%) |
| #19 + TA | 9.4 ± 1.6 | 5/5 (100%) | 5/5 (100%) |

‡= p < 0.0001 compared to wildtype. Initial occlusion refers to the time to first occlusion in those animals that developed any occlusive thrombi. WT = wildtype littermates combined for lines #13 and #19. TA = drinking water contained tranexamic acid (20 mg/ml).

Example 8

Pulmonary Microemboli Model

The following experiment was performed to determine whether the u-PA containing platelets are also effective on the venous side of the circulation and would lead to rapid dissolution of pulmonary microemboli. Previously, the lysis of $^{125}$I-labeled, fibrin microparticles was shown to depend on u-PA expression in the recipient mice as an intravenous infusions of u-PA into u-PA null mice normalized the rate of fibrinolysis (Bdeir, K. et al, cited above). This study determined whether u-PA-containing platelets similarly enhance fibrin clot breakdown.

$^{125}$I-labeled human microemboli, 1.5-3.5$\mu^3$ in size, were prepared as previously described (Bdeir, K. et al, 2000 *Blood* 96:1820-1826). Transgenic and wildtype animals were injected with these particles within 48 hours of preparation. At various time points (2-60 minutes) the animals were euthanized, the lungs removed, washed free of blood, and the amount of $^{125}$I activity measured using a ZM Coulter Counter (Coulter Electronics, Hialeah, Fla.). In other experiments, autoradiograms of lungs were taken from wildtype and transgenic mice 30 minutes after injection of the microemboli by exposing the lungs to X-OMAT film (Kodak, Rochester N.Y.).

Figure 2:
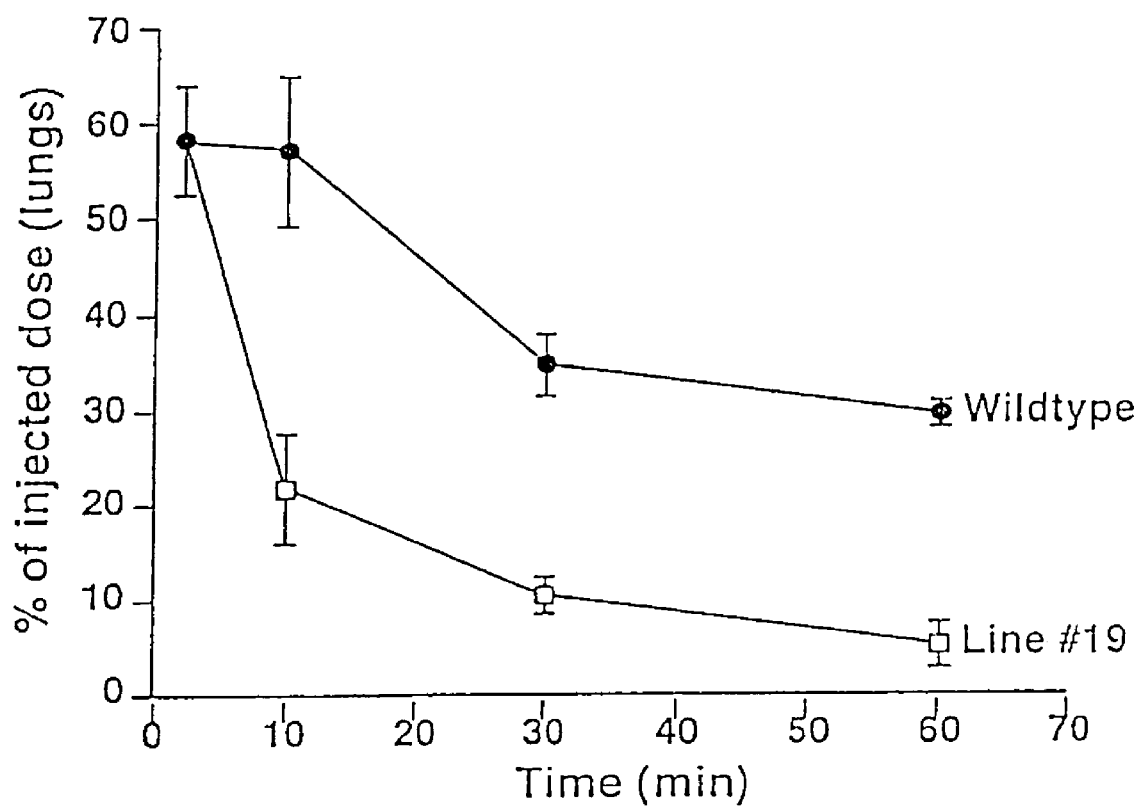
FIG. 2 is a graph of a pulmonary microemboli lysis study. Solid circles show residual labeled microemboli remaining in the lungs of wildtype mice at the indicated times (n=6). Open squares show the residual radioactivity in the lungs of line #19 mice studied in parallel (n=6). Mean±1 SD is shown.

FIG. 2 shows residual labeled microemboli remaining in the lungs of wildtype mice over time and residual radioactivity in the lungs of line #19 mice studied in parallel (n=6). Fibrinolysis was dramatically accelerated in line #19 mice compared to wildtype controls. Differences were already evident at two minutes. By 10 minutes, at a time when there was minimal or no fibrinolysis in wildtype mice, >80% of the clot burden had already been cleared from the lungs of the line #19 mice.

Example 9

Platelet Transfusion/Carotid Artery Studies

Based on the prior experiments that showed that platelet-expressed u-PA both prevented untoward arterial thrombosis and accelerated lysis of venous emboli, this experiment investigated whether transfused u-PA-containing platelets would interfere with thrombus development and stability in wildtype animals.

Platelet transfusions equivalent to ~10% of the total circulating platelets in an animal were given from line #19 animals to wildtype littermate controls prior to exposing the carotid artery to a ferric chloride injury. Surprisingly, wildtype animals that received u-PA-containing platelets were protected against the development of thrombosis to the same extent as line #19 mice themselves (Table 2). Transfusion of buffer only or wildtype platelets into wildtype animals did not prevent the development of occlusive thrombi. As anticipated from the above data, giving wildtype platelets to line #19 mice did not confer resistance to arterial thrombosis.

TABLE 2

Platelet transfusion ferric chloride thrombosis model.

| Founder Line | | Time to initial | Initial | Occluded at |
|---|---|---|---|---|
| Recipient | Donor | occlusion (mins) | occlusion (%) | 30 mins (%) |
| WT | Buffer | 9.3 ± 1.2 | 5/5 (100%) | 5/5 (100%) |
| WT | WT | 8.2 ± 1.4 | 5/5 (100%) | 5/5 (100%) |
| WT | #19 | 12.5 | 1/10 (10%)‡ | 1/10 (0%)‡ |
| WT/TA | #19 | 8.3 ± 1.9 | 5/5 (100%) | 4/5 (80%) |
| WT | #19/TA | 10.5, 22.5 | 2/3 (67%) | 0/3 (0%) |
| #19 | WT | — | 0/3 (0%) | 0/3 (0)% |

‡= $p < 0.0001$ compared to wildtype receiving wildtype platelets. Time to initial occlusion, WT and TA are defined in Table 1. Buffer = gel-filtering buffer.

To test whether protection from thrombosis seen in wildtype animals receiving line #19 platelets was attributable to the released u-PA or to the released degraded alpha-granular proteins, wildtype animals were placed on drinking water containing tranexamic acid. A week later, carotid artery injury was performed on these wildtype mice after they had received an infusion of platelets from the line #19 animals. It was anticipated that platelet-associated plasminogen activation would be inhibited in tranexamic acid-treated recipients leading to loss of protection from thrombosis if released u-PA is the primary mechanism by which line #19 platelets interfere with normal thrombus development. As hypothesized, recipient wildtype animals that had received tranexamic acid lost their resistance to arterial occlusion notwithstanding transfusion of the transgenic platelets, suggesting that the released u-PA contributes significantly to the observed antithrombotic effect of the line #19 platelets. The converse experiment, infusing platelets from a line #19 animal that had been on tranexamic acid for one week to wildtype littermates showed that the infused platelets conferred resistance to arterial thrombosis. These data support the conclusion that line #19 platelets interfere with thrombosis in wildtype animals primarily because ectopically expressed u-PA is released from the donor platelets.

Applicants specifically incorporate by reference D. Kufrin et al, 2003 *Blood,* 102(3):926-933. All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

The invention claimed is:

1. An isolated platelet transformed, transduced, infected or transfected with a nucleic acid molecule comprising a first sequence encoding the transgene urokinase-type plasminogen activator (uPA) under the control of the Platelet factor 4 (PF4) promoter that directs expression and storage of urokinase-type plasminogen activator in granules in said platelet.

2. A method for treating or preventing thrombus formation in a mammal comprising delivering to a mammalian patient a platelet according to claim 1.

3. The method according to claim 2, wherein the platelet produces said uPA at a suitable site in said mammal.

4. The method according to claim 2, wherein said delivering comprises administering said platelet directly into the blood circulation of said mammal.

* * * * *

UNITED STATES PATENT AND TRADEMARK OFFICE
CERTIFICATE OF CORRECTION

| | | |
|---|---|---|
| PATENT NO. | : 7,939,063 B2 | Page 1 of 1 |
| APPLICATION NO. | : 11/581559 | |
| DATED | : May 10, 2011 | |
| INVENTOR(S) | : Douglas B. Cines and Mortimer Poncz | |

It is certified that error appears in the above-identified patent and that said Letters Patent is hereby corrected as shown below:

In the Specification

Column 1, after the heading "STATEMENT REGARDING FEDERALLY SPONSORED RESEARCH OR DEVELOPMENT," the paragraph immediately following is replaced with the following paragraph:

-- "This invention was made with government support under Grant Numbers HL064190 and HL058107 awarded by the National Institutes of Health. The government has certain rights in the invention." --

Signed and Sealed this
Seventeenth Day of August, 2021

Drew Hirshfeld
*Performing the Functions and Duties of the
Under Secretary of Commerce for Intellectual Property and
Director of the United States Patent and Trademark Office*